(12) United States Patent
Hosogoe

(10) Patent No.: US 11,116,385 B2
(45) Date of Patent: Sep. 14, 2021

(54) ENDOSCOPE CAP

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/569,329

(22) PCT Filed: Jul. 18, 2017

(86) PCT No.: PCT/JP2017/025969
§ 371 (c)(1),
(2) Date: Oct. 25, 2017

(87) PCT Pub. No.: WO2018/016487
PCT Pub. Date: Jan. 25, 2018

(65) Prior Publication Data
US 2019/0059702 A1 Feb. 28, 2019

Related U.S. Application Data

(63) Continuation of application No. PCT/JP2017/025996, filed on Jul. 18, 2017.

(30) Foreign Application Priority Data

Jul. 19, 2016 (JP) .............................. JP2016-141762

(51) Int. Cl.
*A61B 1/00* (2006.01)
*A61B 1/018* (2006.01)
*G02B 23/24* (2006.01)

(52) U.S. Cl.
CPC ........ *A61B 1/00098* (2013.01); *A61B 1/0011* (2013.01); *A61B 1/00101* (2013.01);
(Continued)

(58) Field of Classification Search
CPC . A61B 1/00098; A61B 1/00101; A61B 1/018; A61B 1/00137; A61B 1/0008
(Continued)

(56) References Cited

U.S. PATENT DOCUMENTS 5,562,600 A 10/1996 Matsuno
5,569,157 A 10/1996 Nakazawa et al.
(Continued)

FOREIGN PATENT DOCUMENTS

CN 101061940 A 10/2007
CN 101073492 A 11/2007
(Continued)

OTHER PUBLICATIONS

JP2018-139578, "Office Action" dated Nov. 26, 2019, with Machine Translation.
(Continued)

*Primary Examiner* — Alexandra L Newton
(74) *Attorney, Agent, or Firm* — Kilpatrick Townsend & Stockton LLP

(57) ABSTRACT

An endoscope cap with an elevator, which is easily attached to and detached from the distal end of the endoscope, may be provided. An endoscope cap attachable to and detachable from the endoscope, including a lever pivotally provided at a distal end of an insertion part of the endoscope and a pivot part making the lever pivot, comprises a bottomed cylindrical cover having an opening end, the opening end being attachable to and detachable from a distal end of the insertion part of the endoscope; a pedestal fixed to an inside of the cover and having an elevator attachment hole; and an elevator located inside the cover and having an elevator shaft inserted into the elevator attachment hole, the elevator being pivotable around the elevator shaft with respect to the pedestal.

11 Claims, 27 Drawing Sheets

(52) U.S. Cl.
CPC .......... *A61B 1/00137* (2013.01); *A61B 1/018* (2013.01); *G02B 23/2423* (2013.01)

(58) Field of Classification Search
USPC ........................................................ 600/107
See application file for complete search history.

(56) References Cited

U.S. PATENT DOCUMENTS

| | | | |
|---|---|---|---|
| 5,730,701 | A | 3/1998 | Furukawa et al. |
| 5,860,913 | A | 1/1999 | Yamaya et al. |
| 2001/0044570 | A1 | 11/2001 | Ouchi et al. |
| 2004/0006256 | A1 | 1/2004 | Suzuki et al. |
| 2007/0213591 | A1 | 9/2007 | Aizenfeld et al. |
| 2007/0246506 | A1 | 10/2007 | Hamazaki et al. |
| 2007/0270638 | A1 | 11/2007 | Kitano et al. |
| 2017/0000317 | A1* | 1/2017 | Iizuka ...................... A61B 1/00 |
| 2017/0238789 | A1* | 8/2017 | Iizuka ................ A61B 1/00089 |
| 2018/0249894 | A1* | 9/2018 | Kolberg ............ A61B 1/00137 |
| 2018/0317741 | A1* | 11/2018 | Yamaya ................ A61B 1/0008 |

FOREIGN PATENT DOCUMENTS

| | | |
|---|---|---|
| JP | H0576479 | 3/1993 |
| JP | H06237883 A | 8/1994 |
| JP | H06315458 | 11/1994 |
| JP | H07184838 A | 7/1995 |
| JP | H0856900 | 3/1996 |
| JP | H0884700 A | 4/1996 |
| JP | H0975296 | 3/1997 |
| JP | 2002017655 | 1/2002 |
| JP | 2002017665 A | 1/2002 |
| JP | 2004-209137 | 7/2004 |
| JP | 2004-254819 | 9/2004 |
| JP | 2004-255033 | 9/2004 |
| JP | 2005179863 A | 7/2005 |
| JP | 2006020725 | 1/2006 |
| JP | 2006075238 | 3/2006 |
| JP | 2009506824 A | 2/2009 |
| JP | 2009525830 A | 7/2009 |
| JP | 2009240703 A | 10/2009 |
| JP | 2012005533 | 1/2012 |
| JP | 2013-183964 A | 9/2013 |
| JP | 2013199091 A | 10/2013 |
| WO | 2007092636 A2 | 8/2007 |
| WO | 2016021234 A1 | 2/2016 |
| WO | 2017025432 | 2/2017 |
| WO | PCT/JP2017/025969 | 7/2017 |

OTHER PUBLICATIONS

JP2018-139679, "Office Action" dated Dec. 3, 2019, with Machine Translation.
JP2018-139678, "Office Action" dated Nov. 26, 2019, with Machine Translation.
JP2018-139678, Office Action dated May 28, 2019.
JP2018-139679, Office Action dated May 28, 2019.
JP2018-139680, Office Action dated Jun. 25, 2019.
CN201780001267.4, "Chinese Office Action dated Jan. 29, 2019", 8 pages.
JP2018-071833, "Japanese Office Action dated Jan. 29, 2019", 4 pages.
JP Patent Application No. 2017-549355 Office Action, dated Oct. 2, 2018; 3 pages.
JP2020004581, "Notice of Reasons for Refusal" with Machine Translation, dated Mar. 30, 2021, 6 pages.
IN202018021005, "Examination Report", dated Jun. 17, 2021, 5 pages.

* cited by examiner

FIG. 14
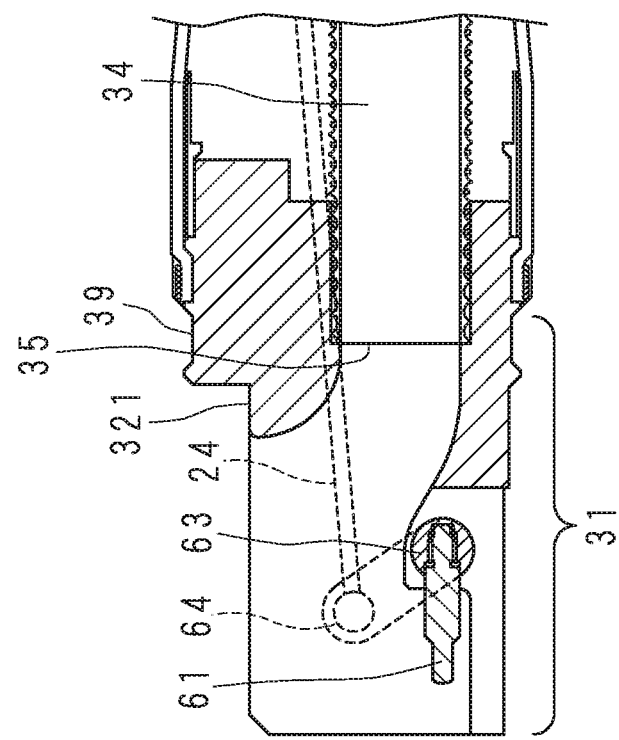
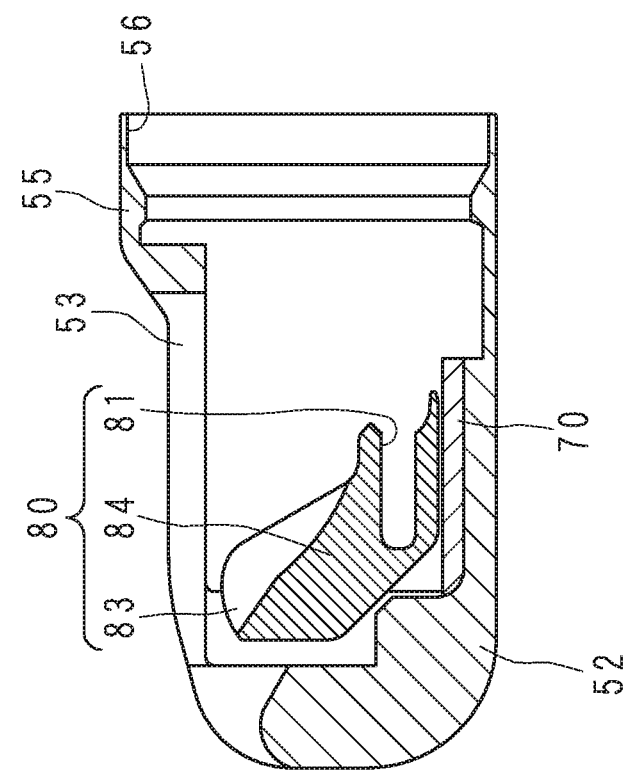

ENDOSCOPE CAP

CROSS-REFERENCE TO RELATED APPLICATIONS

This application is the national phase under 35 U. S. C. § 371 of PCT International Application No. PCT/JP2017/025969 which has an International filing date of Jul. 18, 2017 and designated the United States of America.

FIELD

The present invention relates to an endoscope cap, an endoscope and a method of manufacturing an endoscope cap.

BACKGROUND

An endoscope having an elevator at the distal end of a channel passing through the inside of an insertion part has been used. The elevator is used to bend a treatment tool or the like inserted into the channel and to guide the tool to have a desired orientation.

An endoscope provided with a wall between an elevator and an elevating wire which moves the elevator is disclosed in Japanese Patent Application Laid-Open Publication No. H8-56900 (hereinafter, referred to as Patent Document 1). An endoscope having an elevator mounted to a cap which is detachable from the distal end of an insertion part is disclosed in Japanese Patent Application Laid-Open Publication No. 2002-17655 (hereinafter, referred to as Patent Document 2).

An endoscope in which an elevator, an elevating wire and a cap covering the elevator are detachable from an insertion part is disclosed in Japanese Patent Application Laid-Open Publication No. H6-315458 (hereinafter, referred to as Patent Document 3).

SUMMARY

The endoscope disclosed in Patent Document 1 takes a lot of work in cleaning because of its complicated structure around the elevator. The endoscopes disclosed in Patent Documents 2 and 3 require a lot of trouble in attachment and detachment of the cap.

According to an aspect, an object is to provide an endoscope cap with an elevator which is easily attached to and detached from the distal end of an endoscope.

An endoscope cap attachable to and detachable from an endoscope including a lever pivotally provided at a distal end of an insertion part of the endoscope and a pivot part causing the lever to pivot, comprises: a bottomed cylindrical cover that has an opening end, a window part opened at a side surface and a cutout contiguous to the window part, the opening end being attachable to and detachable from the distal end of the insertion part of the endoscope; a pedestal that is fixed to an inner side of the cover and that has an elevator attachment hole; and an elevator that is located at the inner side of the cover, and that has an elevator shaft inserted into the elevator attachment hole, an elevating part protruding in a direction intersecting the elevator shaft and a lever connection part located at the opening end side of the elevating part and connected to the lever, the elevator being able to pivot around the elevator shaft with respect to the pedestal.

According to an aspect, an endoscope cap with an elevator which is easily attached to and detached from the distal end of the endoscope may be provided.

The above and further objects and features will more fully be apparent from the following detailed description with accompanying drawings.

BRIEF DESCRIPTION OF THE DRAWINGS

FIG. 14 is a section view illustrating the procedure of attaching the cap to the distal end of the insertion part;

DETAILED DESCRIPTION

Embodiment 1

Figure 1:
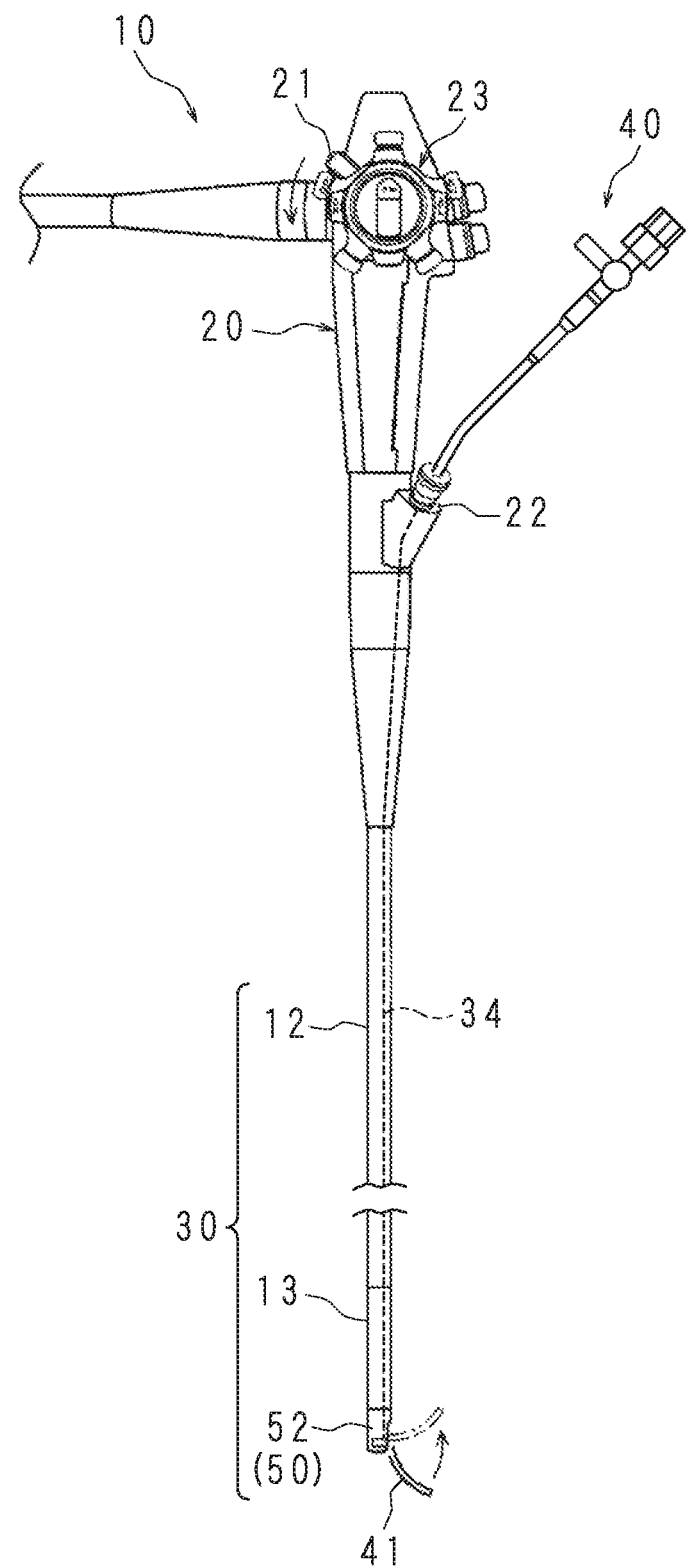
FIG. 1 illustrates an outer appearance of an endoscope.

FIG. 1 illustrates the outer appearance of an endoscope 10. The endoscope 10 according to the present embodiment is a flexible endoscope directed to an upper gastrointestinal tract. The endoscope 10 has an operation part 20 and an insertion part 30. The operation part 20 includes an elevator operation lever 21, a channel inlet 22 and a bending knob 23. The operation part 20 is connected to a video processor, a light source device, a display device and so forth that are not illustrated.

The insertion part 30 is long and has one end connected to the operation part 20. The insertion part 30 has, from the operation part 20 side, a flexible section 12, a bending section 13 and a cap 50. The flexible section 12 is flexible. The bending section 13 bends in response to the operation of the bending knob 23. The cap 50 covers a rigid distal end portion 31 (see FIG. 2) that is contiguous from the bending section 13. The cap 50 is an example of an endoscope cap according to the present embodiment.

In the endoscope 10 according to the present embodiment, the cap 50 may be attached or detached to/from the distal end portion 31. The cap 50 has a cover 52 which is an exterior member and an elevator 80 (see FIG. 2). The detailed structure of the cap 50 will be described later.

In the following description, the longitudinal direction of the insertion part 30 will be referred to as an insertion direction. Likewise, along the insertion direction, the side closer to the operation part 20 will be referred to as a proximal side, whereas the side farther from the operation part 20 will be referred to as a distal side.

Figure 2:
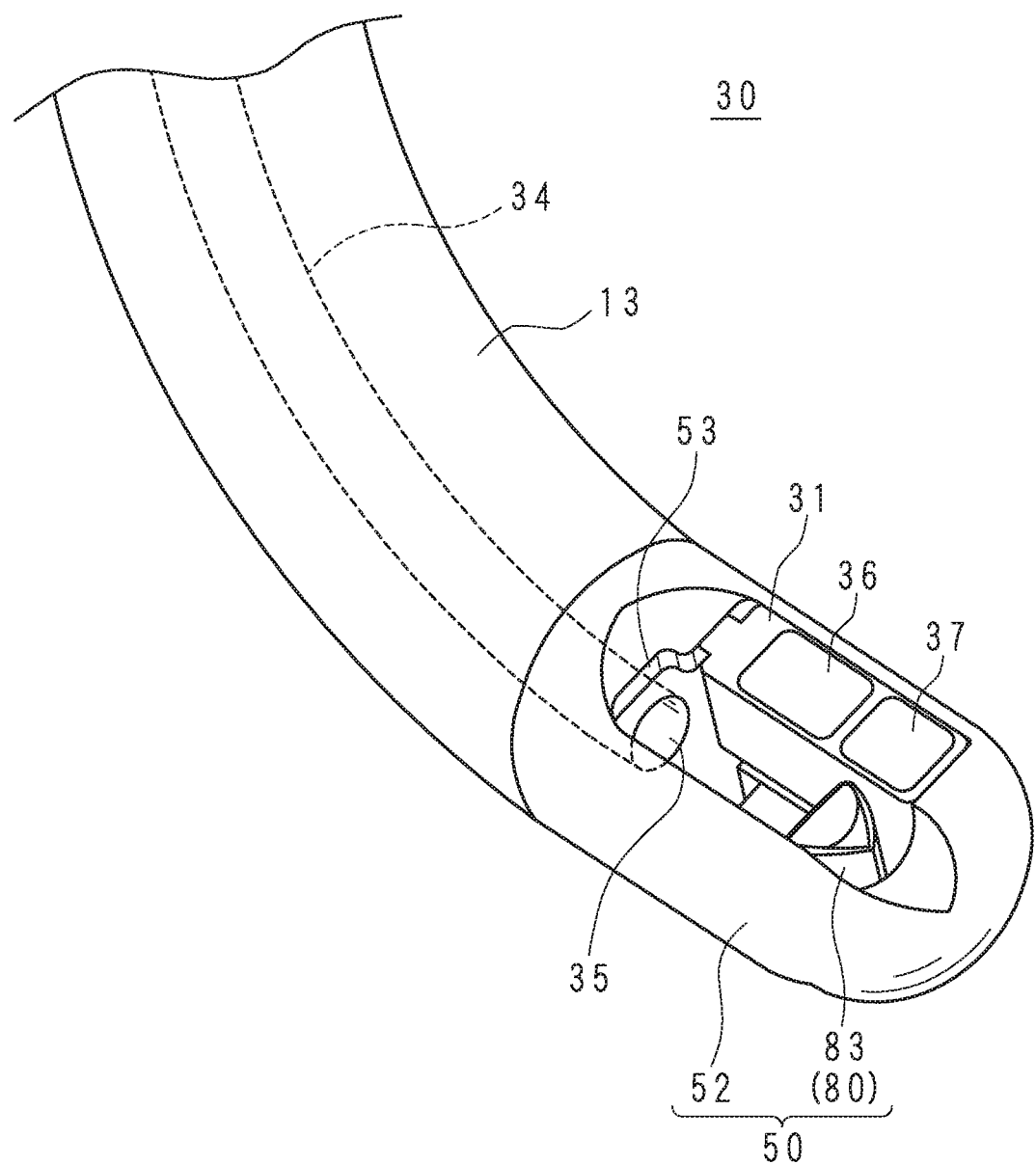
FIG. 2 is a perspective view of a distal end of an insertion part.
Figure 3:
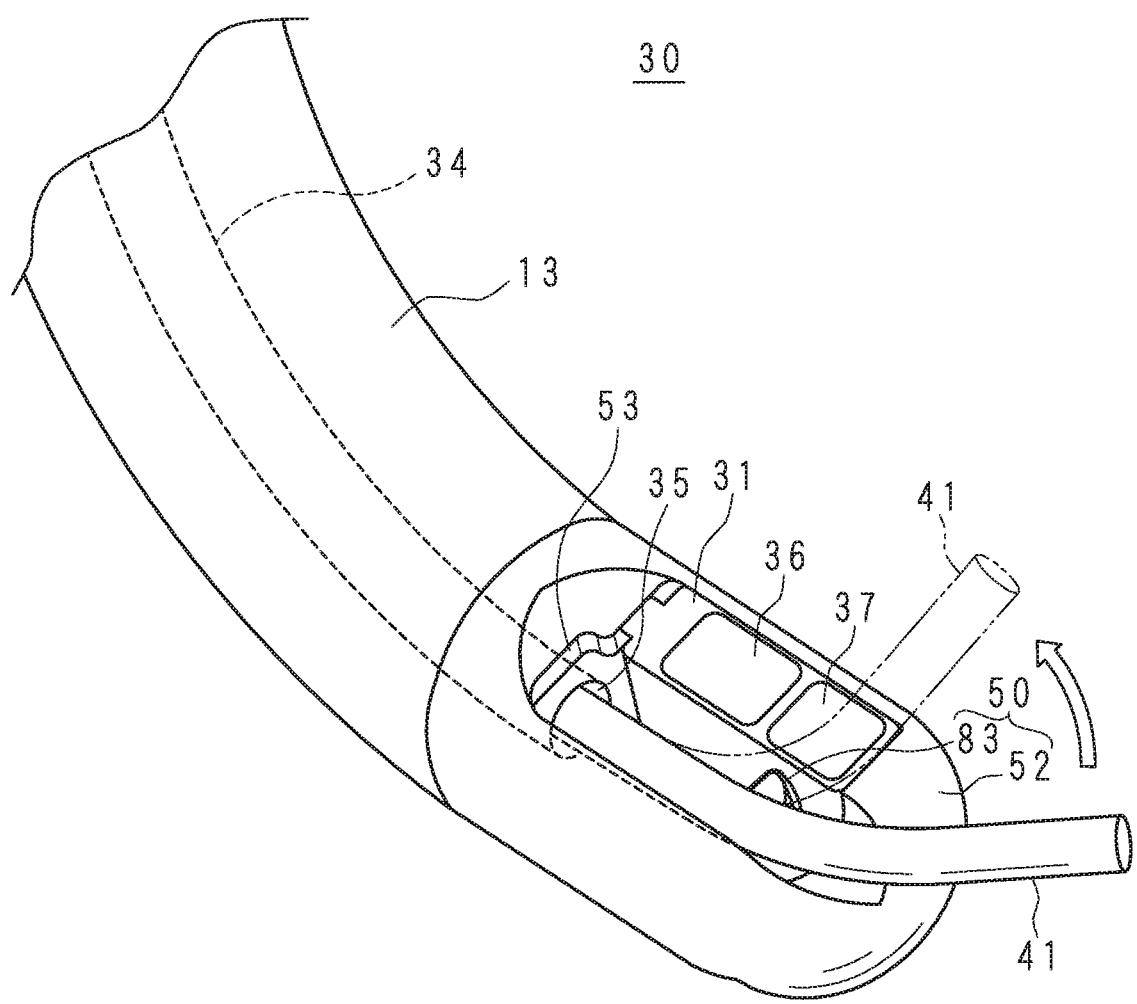
FIG. 3 illustrates a state where a treatment tool tip end protrudes from the distal end of the insertion part.

FIG. 2 is a perspective view of a distal end of the insertion part 30. FIG. 3 illustrates the state where a treatment tool tip end 41 protrudes from the distal end of the insertion part 30. The configuration of the endoscope 10 according to the present embodiment will be described with reference to FIGS. 1 to 3.

A distal end portion 31 located at the distal end of the bending section 13 has, on one side thereof, an observation window 36 and an illumination window 37 that are aligned on one side along the insertion direction. The illumination window 37 is located more toward the distal side than the observation window 36. The distal end portion 31 has a channel outlet 35 at the proximal side on the other side thereof. An elevating part 83 is disposed at the distal side of the channel outlet 35. The cover 52 which covers the distal end portion 31 has a substantially rectangular window part 53 at a portion corresponding to the observation window 36, illumination window 37 and elevating part 83.

The illumination window 37 directs the illumination light emitted from a light source device (not illustrated). Through the observation window 36, it is possible to optically observe the area irradiated with the illumination light. The endoscope 10 according to the present embodiment is of a so-called side view type, in which a viewing direction for optical observation is a direction intersecting the insertion direction. The endoscope 10 may also be of a forward oblique view type with a viewing direction somewhat inclined toward the distal end or a backward oblique view type with a viewing direction somewhat inclined toward the proximal end.

The channel inlet 22 and the channel outlet 35 are connected with each other by a channel 34 running through the inner side of the flexible section 12 and the bending section 13. The treatment tool 40 may be inserted through the channel inlet 22 from the treatment tool tip end 41, to protrude the treatment tool tip end 41 from the channel outlet 35.

As illustrated by the solid line in FIG. 3, the treatment tool tip end 41 protrudes while curving gently over the elevating part 83. If the elevator operation lever 21 is operated as illustrated by the arrow in FIG. 1, a lever 60 moves as described later, and an elevator 80 also moves in conjunction with the lever 60. As the elevator 80 moves, the treatment tool tip end 41 located over the elevator 80 is bent toward the proximal side, i.e. the operation part 20 side, as indicated by the arrows in FIGS. 1 and 3. The movement of the treatment tool tip end 41 is photographed by an image sensor (not illustrated) or the like through the observation window 36, and is displayed on a display device (not illustrated).

The treatment tool 40 is an instrument for treatment, for example, a high-frequency knife, forceps or contrast tube. The instrument to be inserted into the channel 34 is not limited to the instrument for treatment. For example, an instrument for observation such as an ultrasound probe or ultra-slim endoscope may also be inserted into the channel 34 and used. In the following description, the treatment tool 40 includes an instrument for observation.

Figure 4:
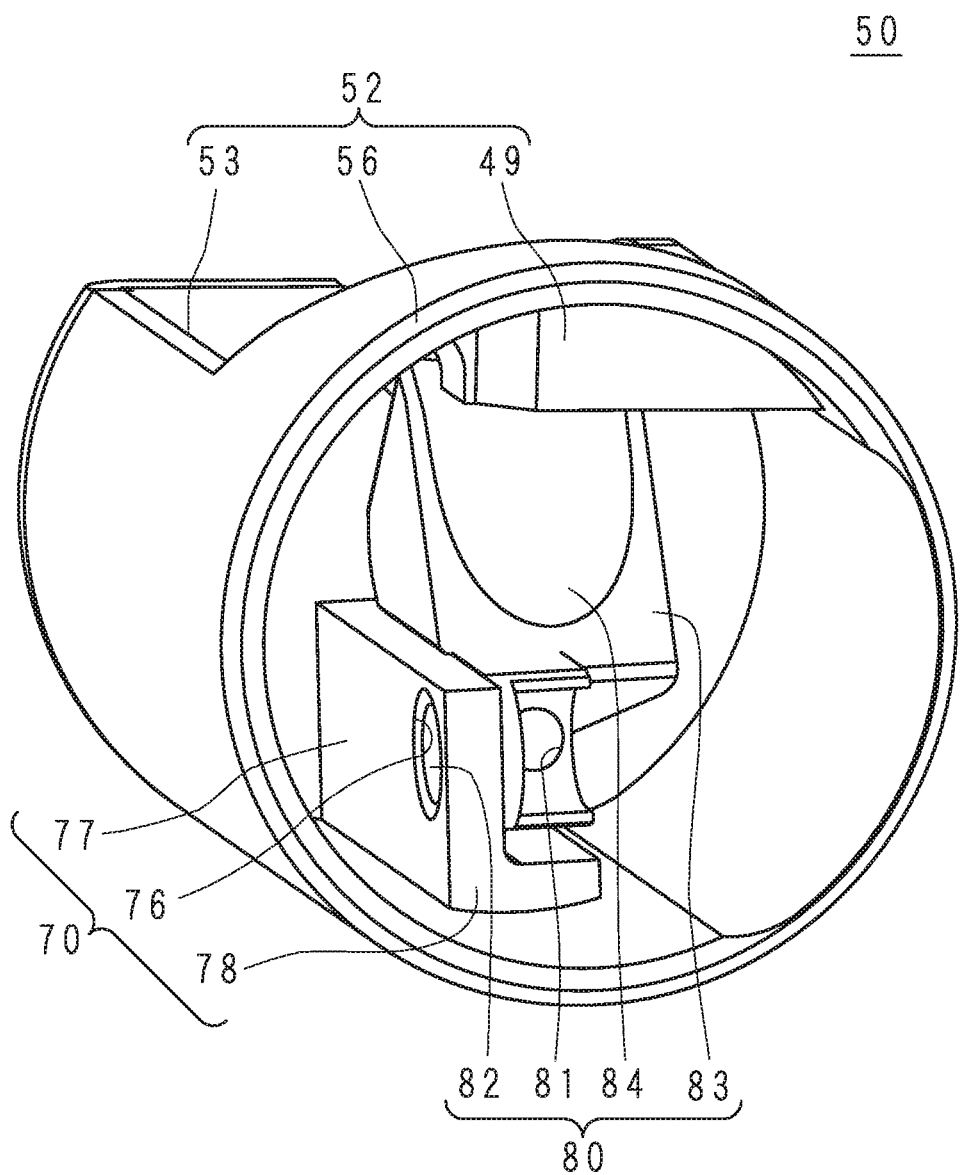
FIG. 4 is a perspective view of a cap.

FIG. 4 is a perspective view of a cap 50. FIG. 4 is a perspective view of a cap 50 when viewed from the attachment side to the endoscope 10. The cap 50 has a cover 52, a pedestal 70 and an elevator 80. The cover 52 has a bottomed cylindrical shape having an opening end 56 at one end thereof and a bottom at the other end thereof. The cover 52 has, at the opening end 56 side of the window part 53, a protrusion 49 which protrudes inward.

The pedestal 70 has a first wall 77 rising toward the window part 53 from the inner surface of the cover 52 that is opposed to the window part 53, and a second wall 78 extending from the first wall 77 on the cover 52 side along the inner surface of the cover 52. The first wall 77 has the shape of a plate with its wide surface being parallel to the axial direction of the cover 52.

The pedestal 70 has an elevator attachment hole 76 penetrating through the first wall 77. The pedestal 70 is fixed to the inner surface of the cover 52 by adhesion or welding while the elevator 80 is pivotally attached to the elevator attachment hole 76. The pivot here means rotary motion within a predetermined angle range.

Figure 5:
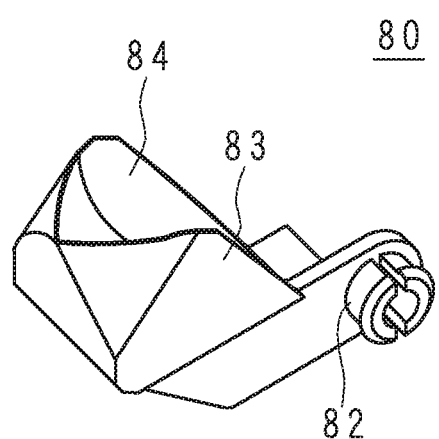
FIG. 5 is a perspective view of an elevator.

FIG. 5 is a perspective view of the elevator 80. The configuration of the elevator 80 will be described with reference to FIGS. 4 and 5. The elevator 80 has an elevator shaft 82, an elevating part 83 and a lever connection part 81. The elevator shaft 82 is a columnar shaft with an expanding slot. The elevator shaft 82 has, at an end thereof, a retainer with a diameter one size larger than that of the elevator shaft 82. The elevating part 83 is disposed in a direction intersecting the central axis of the elevator shaft 82. The elevating part 83 has, at one surface thereof, a spoon-shaped recess 84 which is wider at a side distant from the elevator shaft 82.

The lever connection part 81 is located at the elevator shaft 82 side of the elevating part 83. The lever connection part 81 is a round hole opened at the inner surface of a cylindrical surface that is coaxial with the elevator shaft 82 so as to have an orientation intersecting the elevator shaft 82. More specifically, the central axis of the elevator shaft 82 is orthogonal to the central axis of the lever connection part 81. The lever connection part 81 may be a rectangular hole, an elliptical hole or the like. The lever connection part 81 may or may not penetrate through the elevating part 83. In the following description, the lever connection part 81 of a concave shape may also be referred to as a connection concave part.

The elevator shaft 82 is inserted into the elevator attachment hole 76. The elevator 80 may pivot around the elevator shaft 82 with respect to the pedestal 70. The retainer located at an end of the elevator shaft 82 prevents the once inserted elevator shaft 82 from coming off the elevator attachment hole 76. The recess 84 is opposed to the window part 53.

An assembly method for the cap 50 will be described with reference to FIGS. 4 and 5. First, the elevator 80 is attached to the pedestal 70 so as to be able to pivot. More specifically, the elevator shaft 82 is inserted into the elevator attachment hole 76. Subsequently, the pedestal 70 is fixed to the inner surface of the cover 52. More specifically, the pedestal 70 in which adhesive is applied to one surface of the second wall 78 is inserted into the inner surface of the cover 52 through the opening end 56 side. The adhesive is cured while the surface of the second wall 78 applied with the adhesive is pressed against the inner surface of the cover 52. The direction of inserting the elevator shaft 82 into the elevator attachment hole 76 intersects with the direction of inserting the pedestal 70 into the cover 52.

Figure 6:
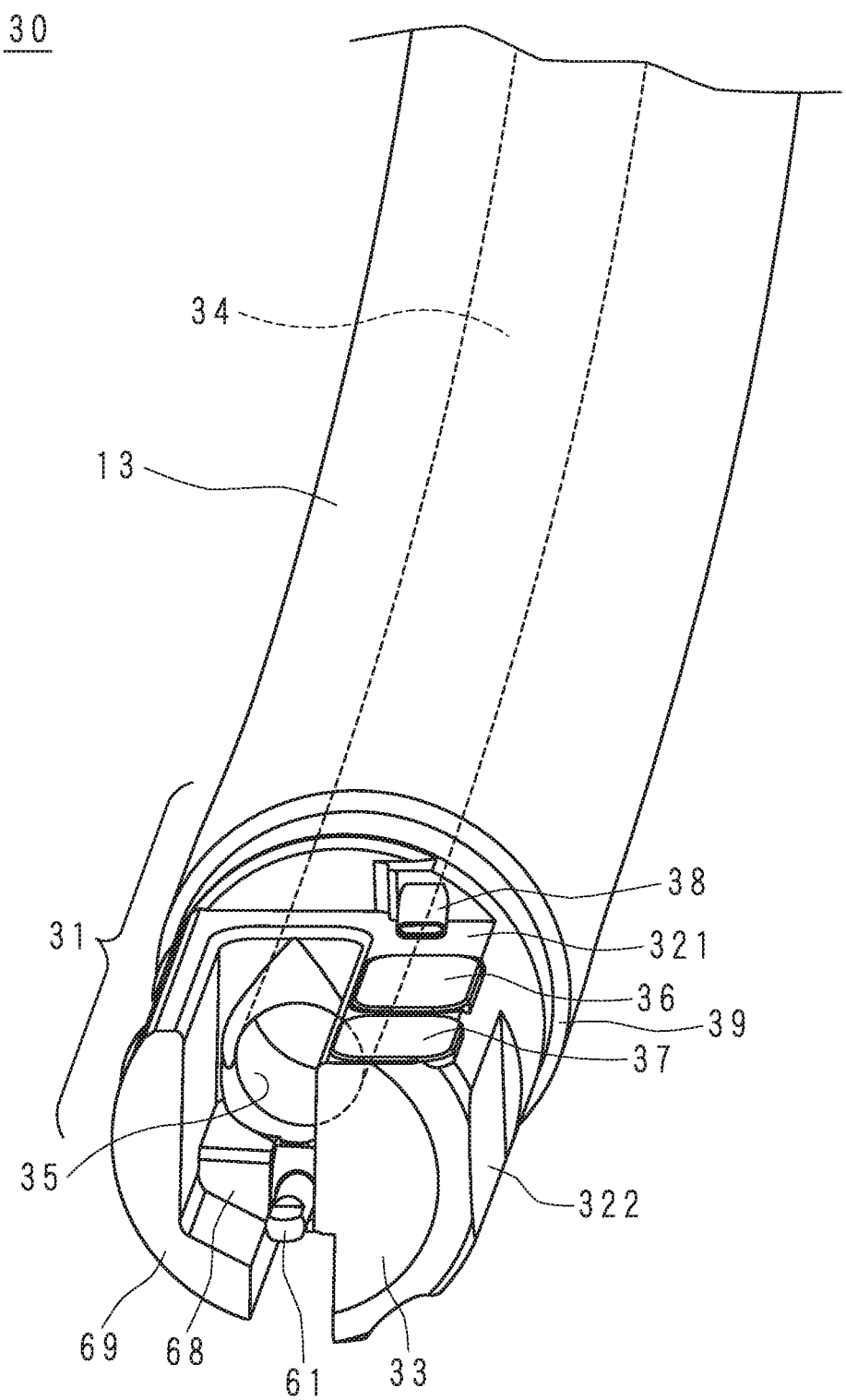
FIG. 6 is a perspective view of the distal end of the insertion part before the cap is attached.

FIG. 6 is a perspective view of the distal end of the insertion part 30 before the cap 50 is attached. The distal end portion 31 has a substantially columnar shape, and is divided into an optics housing 33 and a lever chamber 69 by a groove formed from the distal side to the proximal side at a position offset from the center. The channel outlet 35 is opened at the bottom of the groove. A bar-like elevator connection part 61 is exposed near the channel outlet 35. The elevator connection part 61 will be described later.

The distal end portion 31 has a first planar part 321 along the longitudinal direction of the insertion part 30. At the optics housing 33 side of the first planar part 321, the observation window 36 and the illumination window 37 are disposed. At the proximal side of the observation window 36, a nozzle 38 for injecting water and air to the observation window 36 to clean the observation window 36 is provided. At the outside of the optics housing 33, a second planar part 322 is provided.

The lever chamber 69 is hollow. The lever chamber 69 has a support wall 68 on the optics housing 33 side. The distal end portion 31 has a cap fixing groove 39 at the outer periphery thereof on the proximal side.

Figure 7:
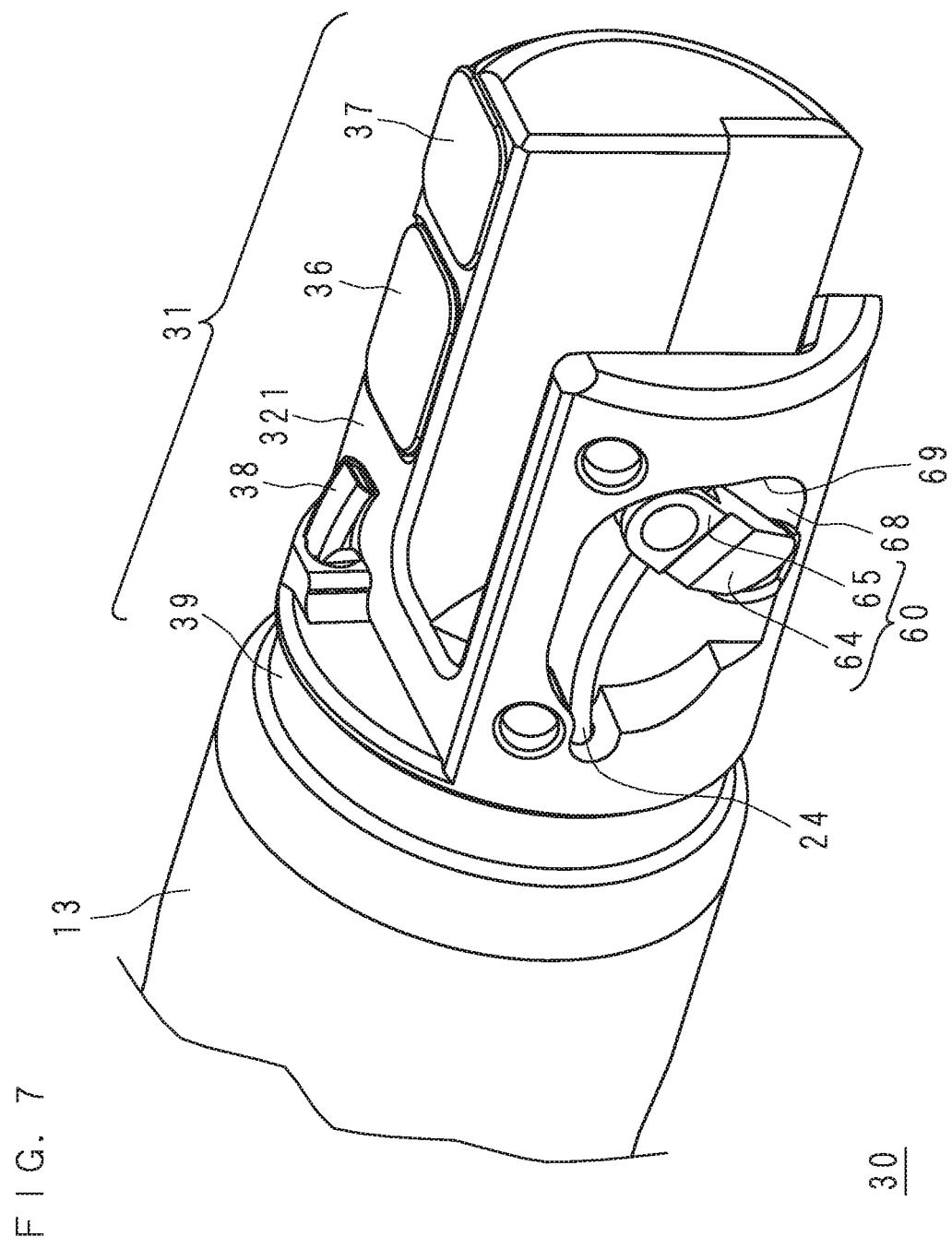
FIG. 7 is a perspective view of the distal end of the insertion part before the cap is attached.

FIG. 7 is a perspective view of the distal end of the insertion part 30 before the cap 50 is attached. FIG. 7 illustrates a state where a lever chamber lid 67 (see FIG. 11) is removed so as to show the inside of the lever chamber 69. A pivot connection part 64 and a wire fixing part 65 are accommodated inside the lever chamber 69. The wire fixing part 65 is connected to an end of the elevating wire 24.

The elevating wire 24 passes through the insertion part 30 and is connected to the elevator operation lever 21 (see FIG. 1). More specifically, the elevating wire 24 is inserted into a guide tube (not illustrated) having an inner diameter somewhat larger than the outer diameter of the elevating wire 24. The guide tube (not illustrated) penetrates through the insertion part 30 along the longitudinal direction. Thus, the distal end of the elevating wire 24 moves back and forth in conjunction with the operation of the elevator operation lever 21. The elevating wire 24 is an example of the pivot part according to the present embodiment. The elevating wire 24 is operated remotely by the elevator operation lever 21.

Figure 8:
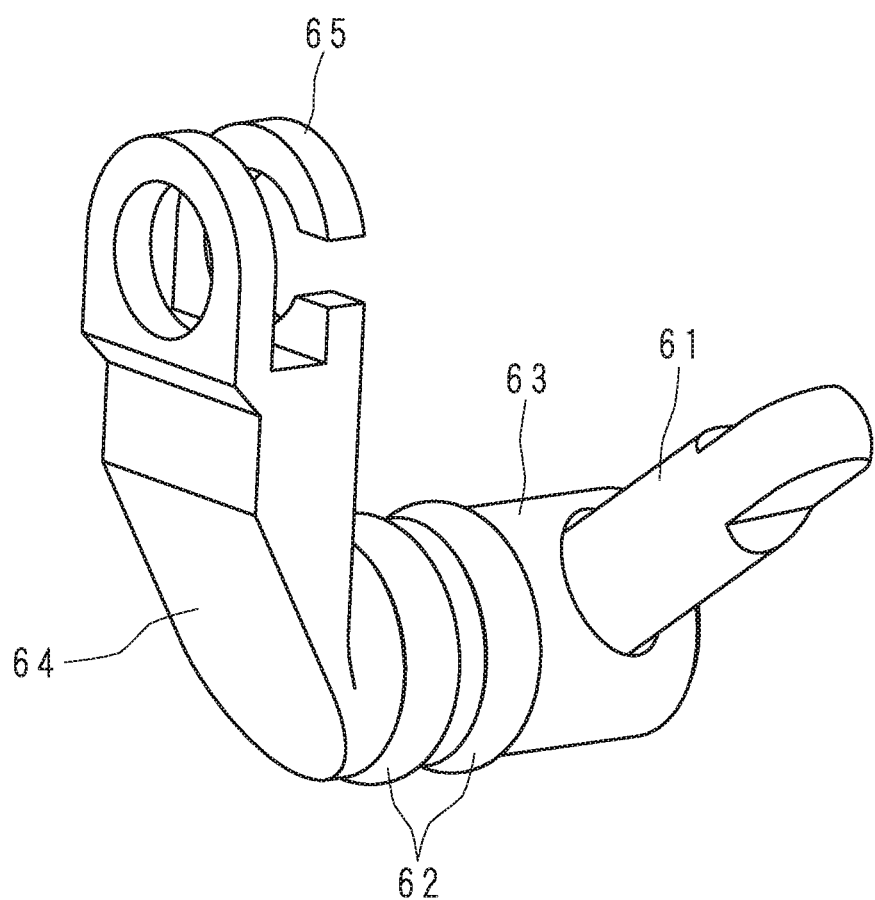
FIG. 8 is a perspective view of a lever.

FIG. 8 is a perspective view of a lever 60. The lever 60 has a lever shaft 63, an elevator connection part 61, a pivot connection part 64, a wire fixing part 65 and two O-rings 62.

The lever shaft 63 is a columnar shaft. The columnar elevator connection part 61 protrudes from the side surface of the lever shaft 63 in a direction intersecting the central axis of the lever shaft 63. From an end of the lever shaft 63, the pivot connection part 64 protrudes in a direction intersecting the central axis of the lever shaft 63, which is different from the protruding direction of the elevator connection part 61. A wire fixing part 65 having an expanding slot is provided at an end of the pivot connection part 64. Two O-rings 62 are fixed at a portion of the lever shaft 63 that is located between the elevator connection part 61 and the pivot connection part 64.

Figure 9:
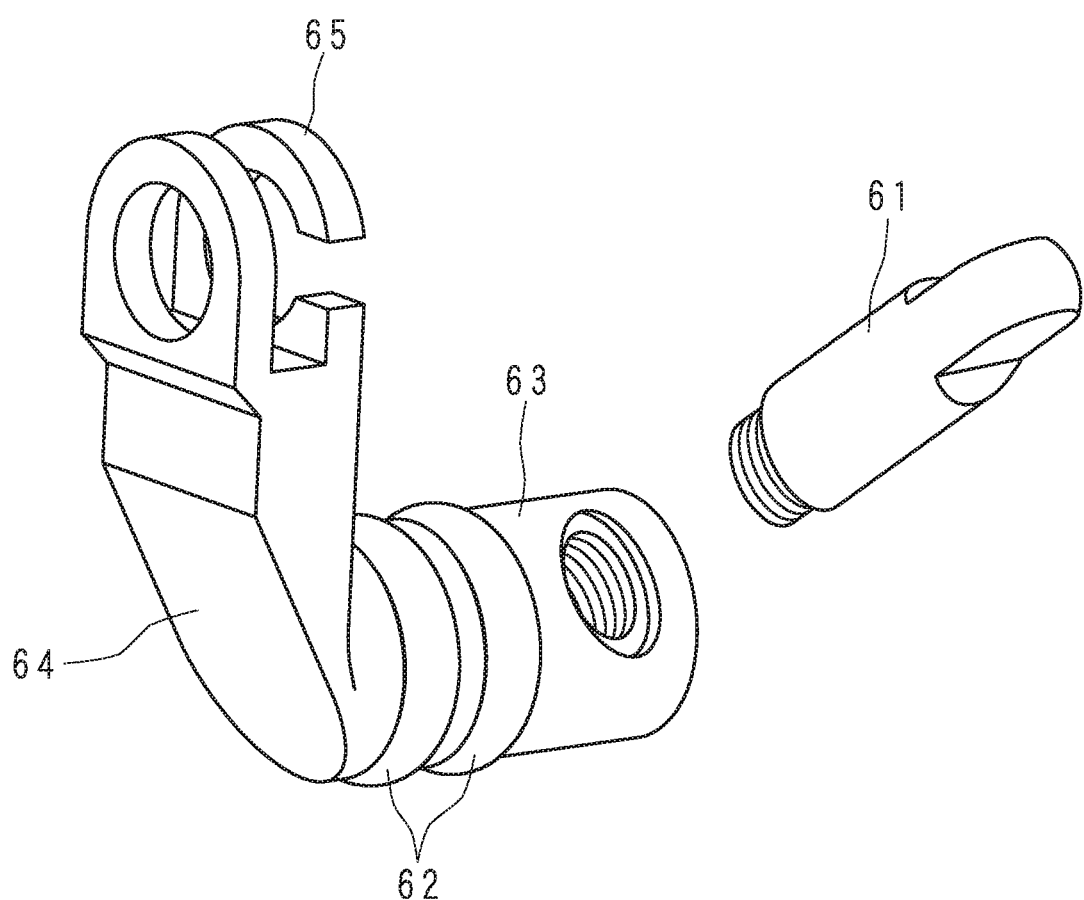
FIG. 9 is an exploded perspective view of the lever.

FIG. 9 is an exploded perspective view of the lever 60. The elevator connection part 61 has a male thread at one end thereof. The lever shaft 63 has a female thread at a side surface thereof. After the lever shaft 63 that received the O-rings 62 is inserted into the hole opened at the support wall 68, the male thread of the elevator connection part 61 is coupled with the female thread of the lever shaft 63, so that the lever 60 is pivotally supported by the support wall 68. By holding and rotating the planar part located at the end of the elevator connection part 61 with a tool such as needle-nose pliers, the elevator connection part 61 and the lever shaft 63 may securely be coupled with each other.

Figure 10:
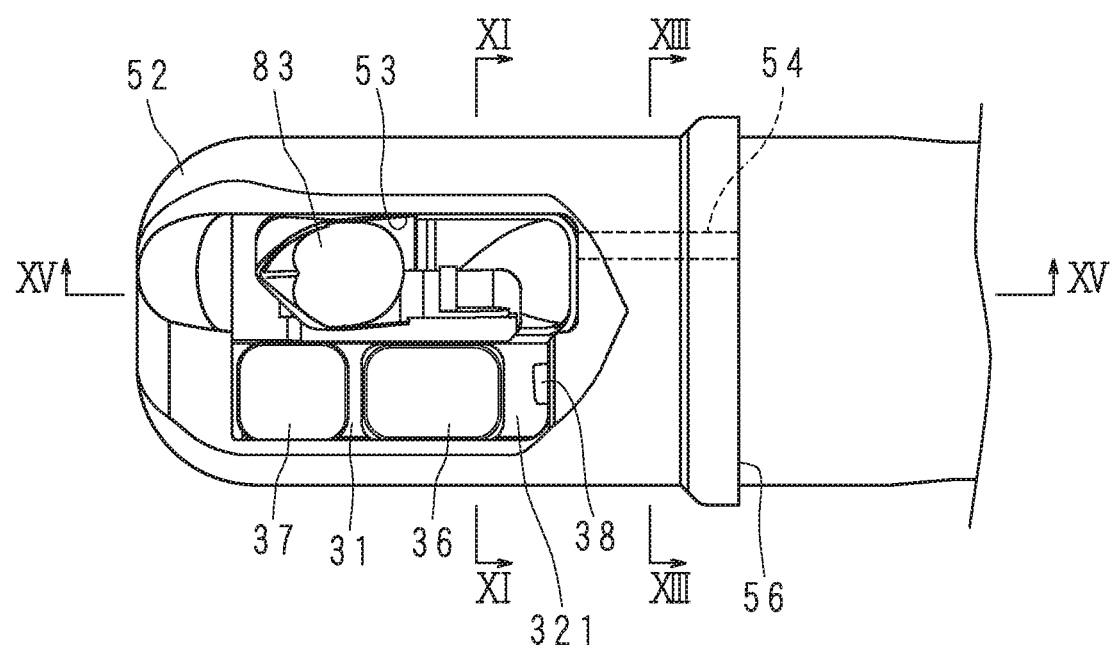
FIG. 10 is a side view of the distal end of the insertion part.

FIG. 10 is a side view of the distal end of the insertion part 30. FIG. 10 illustrates the distal end of the insertion part 30 to which the cap 50 is attached when viewed from the window part 53 side. The cap 50 is fixed to the insertion part 30 by being pressed from the distal side of the distal end portion 31. The end face of the lever chamber 69 on the distal side abuts the bottom of the cap 50. The observation window 36, the illumination window 37 and the elevating part 83 are seen inside the window part 53.

Figure 11:
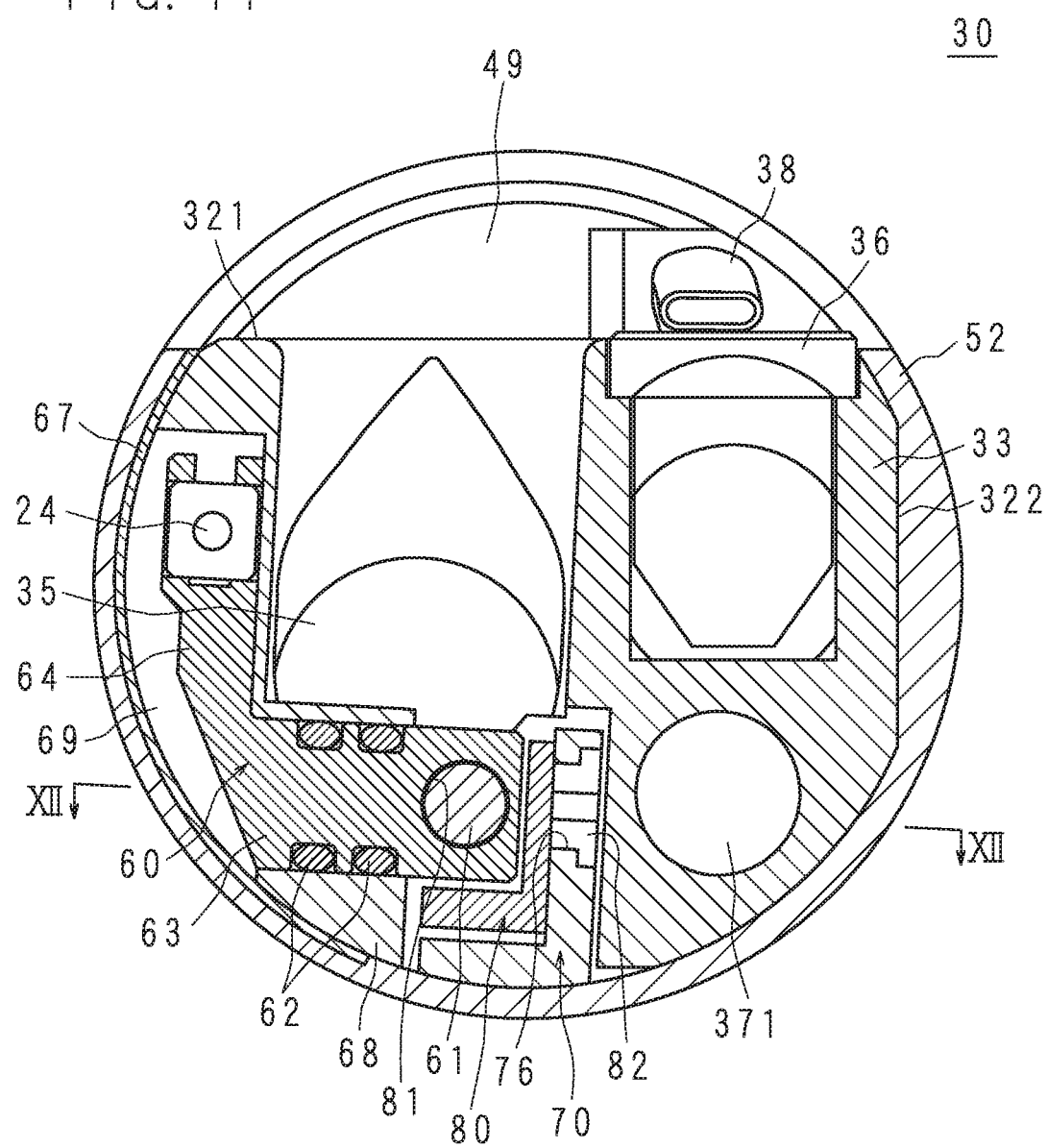
FIG. 11 is a section view of the insertion part taken along the line XI-XI in FIG. 10.

FIG. 11 is a section view of the insertion part 30 taken along the line XI-XI in FIG. 10. The lever chamber 69 is sealed with the lever chamber lid 67. A hole through which the lever shaft 63 penetrates the support wall 68 is sealed with the two O-rings 62. The structure described above prevents water or the like from intruding into the lever chamber 69.

An observation optical system such as lens is disposed under the observation window 36 in FIG. 11. A video image photographed by an image sensor (not illustrated) via the observation optical system is processed by a video processor (not illustrated) and is displayed on a display device.

A light guide fiber 371 is disposed under the observation optical system in FIG. 11. The light guide fiber 371 is connected to the illumination window 37. The light guide fiber 371 guides illumination light from a light source device (not illustrated) to the illumination window 37.

The cover 52 has a planar part corresponding to the second planar part 322 at the inner surface thereof. The second planar part 322 abuts the planar part of the cover 52 so as to prevent the cap 50 from rotating.

Figure 12:
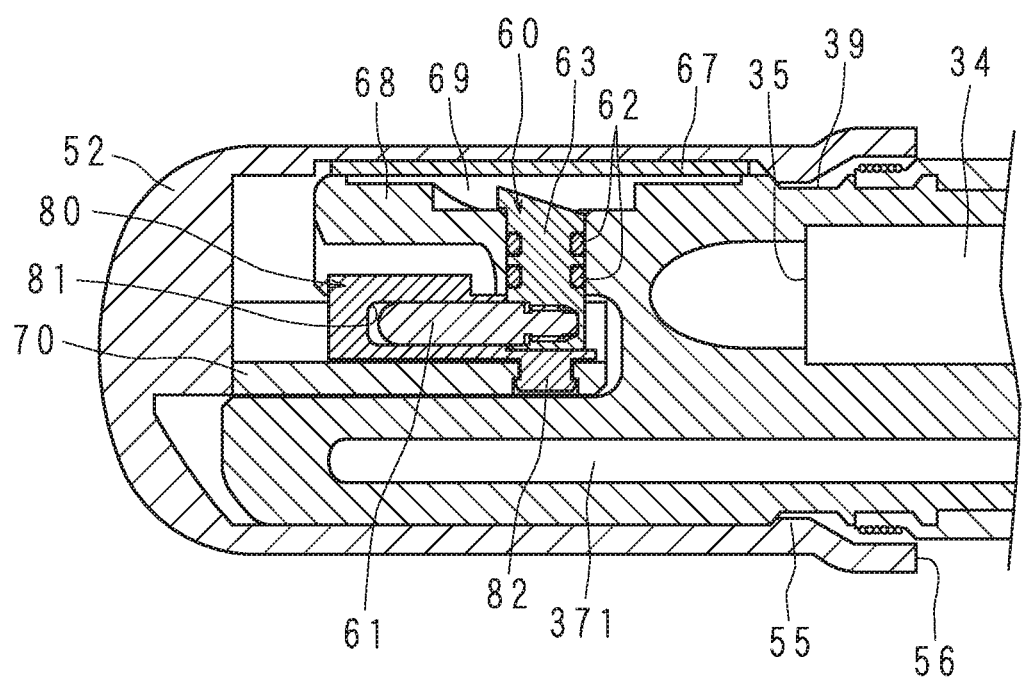
FIG. 12 is a section view of the insertion part taken along the line XII-XII in FIG. 11.

FIG. 12 is a section view of the insertion part 30 taken along the line XII-XII in FIG. 11. The XII-XII section is a cross section passing the central axis of the lever shaft 63 and the central axis of the elevator shaft 82 along the longitudinal direction of the insertion part 30. As illustrated in FIGS. 11 and 12, the central axis of the lever shaft 63 and the central axis of the elevator shaft 82 are coaxially arranged. The lever 60 is provided at the distal end of the insertion part 30 of the endoscope 10 so as to be able to pivot around the lever shaft 63.

The elevator connection part 61 is inserted into the lever connection part 81. The elevator connection part 61 and the lever connection part 81 connect the lever 60 and the elevator 80 with each other. That is, in the case where the lever 60 pivots around the lever shaft 63, the elevator 80 also pivots integrally with the lever 60. Since the central axis of the lever shaft 63 and the central axis of the elevator shaft 82 are coaxially arranged, the elevator 80 smoothly operates together with the lever.

As illustrated above, when the cap 50 is mounted to the distal end portion 31 of the endoscope 10, the elevator 80 is connected to the lever 60. Connection here means the state where the elevator 80 and the lever 60 pivot together if the lever 60 pivots.

In the following description, the elevator connection part 61 having the shape of a projection as illustrated in FIG. 12 may also be referred to as an elevator projection. The elevator projection has a shape which may be inserted into the connection concave part illustrated with reference to FIG. 5.

The cover 52 has, at the inner surface thereof, an attachment projection 55 extending along the edge of the opening end 56. The attachment projection 55 is inclined more gently on the opening end 56 side compared to the bottom side of the cover 52. The attachment projection 55 is engaged with the cap fixing groove 39 formed at an outer periphery of the distal end portion 31.

Because of the gentle inclination on the opening end 56 side, fitting of the attachment projection 55 into the cap fixing groove 39 is relatively easy when the cap 50 is pressed onto the distal end of the insertion part 30. Since the inclination on the bottom side is steep, on the other hand, the cap 50 that had been once fixed is unlikely to come off the insertion part 30. After the cap 50 is pressed onto the distal end of the insertion part 30, a medical tape or the like may be wound around the opening end 56 of the cap 50 as well as the insertion part 30. This can further secure the fixed cap 50.

Figure 13:
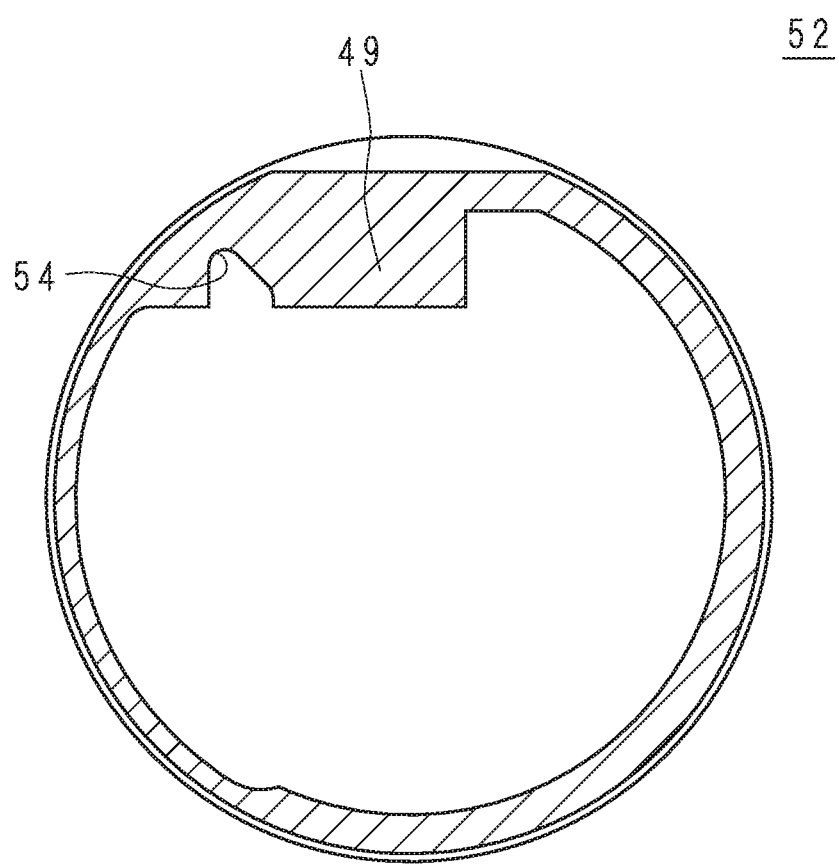
FIG. 13 is a section view of the cover taken along the line XIII-XIII in FIG. 10.

FIG. 13 is a section view of the cover 52 taken along the line XIII-XIII in FIG. 10. In FIG. 13, members other than the cover 52 are not illustrated. The surface of the protrusion 49 that faces the center of the cover 52 is a flat surface. The first planar part 321 abuts the protrusion 49 so as to prevent the cap 50 from rotating.

The cover 52 has a cutout 54 having a substantially triangular cross section at the inner surface thereof. As indicated by the broken lines in FIG. 10, the cutout 54 is a groove formed between the edge of the window part 53 and the opening end 56.

FIG. 14 is a section view illustrating the procedure of attaching the cap 50 to the distal end of the insertion part 30. The elevator operation lever 21 is operated to direct the elevator connection part 61 toward the distal end of the insertion part 30. The elevator 80 in the cap 50 directs the lever connection part 81 toward the opening end 56.

In this state, the cap 50 is pressed onto the distal end portion 31 from the distal side. The cover 52 temporarily expands so that the attachment projection 55 is engaged into the cap fixing groove 39. This fixes the cap 50 to the distal end portion 31. As the elevator connection part 61 fits into the lever connection part 81, the lever 60 and the elevator 80 may pivot in an integrated manner. As described earlier, the end face of the lever chamber 69 on the distal side abuts the bottom of the cover 52, the first planar part 321 abuts the protrusion 49, and the second planar part 322 abuts the flat surface at the inner surface of the cover 52. This structure prevents the cap 50 from rotating and rattling.

Figure 15:
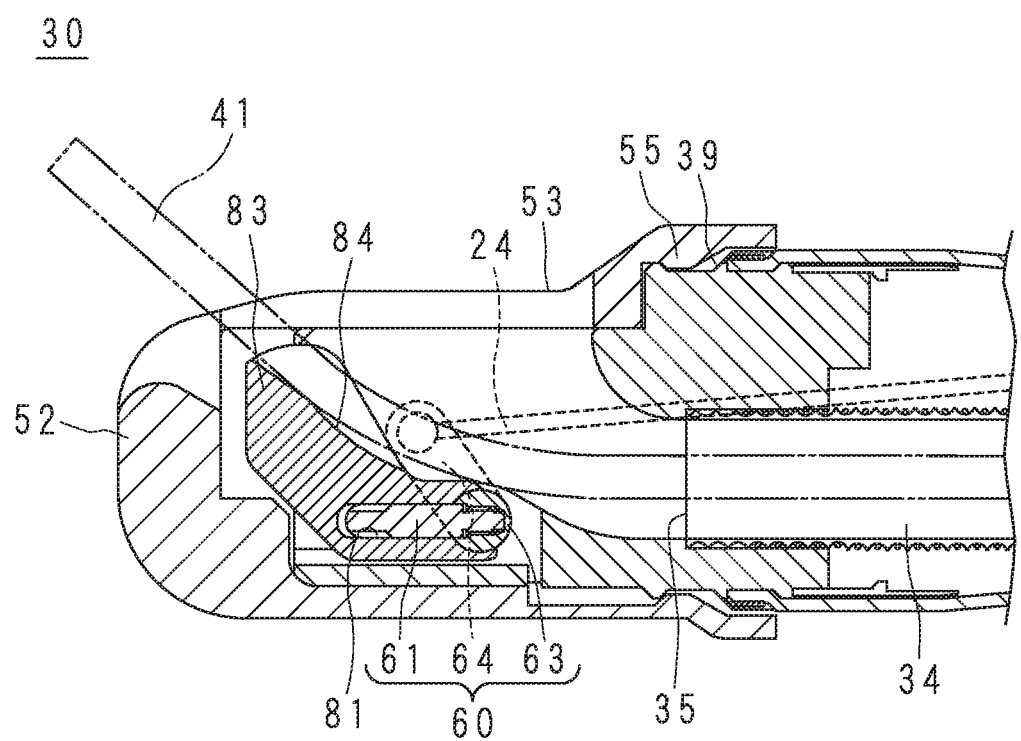
FIG. 15 is a section view of the insertion part taken along the line XV-XV in FIG. 10.
Figure 16:
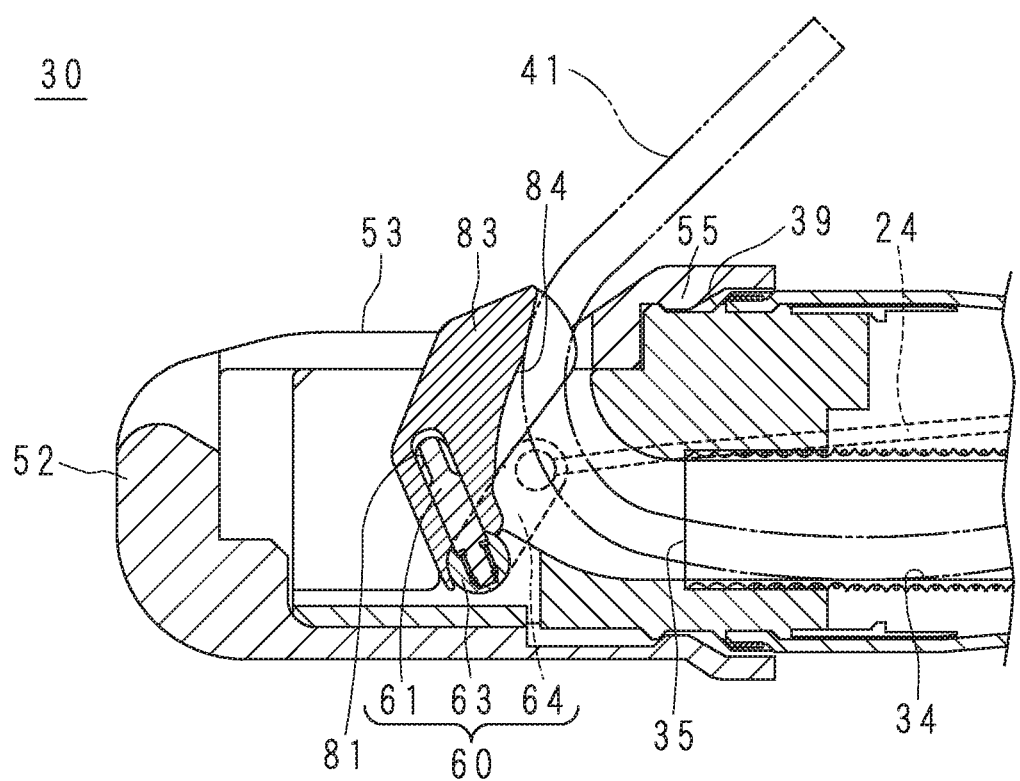
FIG. 16 is a section view of the endoscope in which an elevator is elevated.

FIG. 15 is a section view of the insertion part 30 taken along the line XV-XV in FIG. 10. FIG. 16 is a section view of the endoscope 10 in which the elevator 80 is elevated. The movement of the elevator 80 will be described with reference to FIGS. 15 and 16.

In the state illustrated in FIG. 15, the elevator 80 is accommodated inside the cover 52. The recess 84 is located at a position that allows the treatment tool tip end 41 protruding from the channel outlet 35 to bend gently upward in FIG. 15.

As the elevator operation lever 21 moves, the elevating wire 24 connected to the elevator operation lever 21 is pulled toward the proximal side. Being pulled by the elevating wire 24, the lever 60 pivots around the lever shaft 63. Since the elevator connection part 61 is connected to the lever connection part 81, the elevator 80 also pivots to rise together with the lever 60. As a result, the distance between the elevator 80 and the window part 53 changes.

FIG. 16 illustrates the state where the elevator 80 pivots. Being pushed by the elevator 80, the treatment tool tip end 41 protruding from the channel outlet 35 is bent toward the proximal side. The pivoting movement for the elevator 80 to rise as illustrated in FIG. 16 may also be referred to as "the elevator 80 is elevated" in the description below. The bending of the treatment tool tip end 41 by being pushed by the elevated elevator 80 may also be referred to as "the treatment tool 40 is elevated" in the description below. The operation of the elevator operation lever 21 may adjust the degree of elevation of the treatment tool 40.

A method of using the endoscope 10 according to the present embodiment will now be summarized. The endoscope 10 is stored in a state where the cap 50 is removed and is subjected to cleaning or the like. The cap 50 is provided in a sterilized package. The user takes out the cap 50 from the sterilized package and attaches the cap 50 to the distal end portion 31 of the endoscope 10.

The user inserts the insertion part 30 through the mouth of a subject to be examined. While viewing a video image photographed via the observation window 36, the user guides the distal end of the insertion part 30 to a target site. The user inserts the treatment tool 40 or the like according to a purpose through the channel inlet 22. After confirming that the treatment tool tip end 41 protrudes from the distal end of the insertion part 30 and is located near the target site, the user operates the elevator operation lever 21 to guide the treatment tool tip end 41 to the target site. The user performs a necessary treatment or the like and then pulls out the treatment tool 40 from the channel 34. The user pulls out the endoscope 10 from the subject, and terminates the examination or treatment.

The cover 52 may easily be detached by breaking it through the cutout 54. For example, the user may insert a finger or the like through the window part 53 and break the cover 52 while rolling up the cover 52 outward along the cutout 54 toward the opening end 56. The cap 50 according to the present embodiment is so-called single use, and is discarded after one use.

The user performs a process such as cleaning on the endoscope 10 after the cap 50 is removed, to prepare for the next use. As illustrated in FIG. 6, the endoscope 10 after the cap 50 is detached has no elevator 80. The elevator connection part 61 used when the elevator 80 is fixed is exposed at the distal end portion 31, as illustrated in FIG. 6. Since the lever chamber 69 is sealed with the lever chamber lid 67 and the O-rings 62, no body fluid or the like is adhered to the path of the elevating wire 24.

It is therefore possible to provide the endoscope 10 that has short process time between cases and that may efficiently be put into practice, since no special cleaning work or the like is necessary for cleaning the complicated structure around the elevator 80 and the elevating wire 24.

The endoscope 10 according to the present embodiment is provided with the elevator 80 and is of the side view type, which makes it suitable for diagnosis and treatment of duodenum and pancreaticobiliary duct areas. In particular, for the case of performing procedures such as endoscopic retrograde cholangio pancreatography (ERCP), endoscopic sphincterotomy (EST), endoscopic biliary drainage (EBD) and so forth, the endoscope 10 according the present embodiment is suitable. This is because, in these procedures, treatment or the like is performed by guiding the treatment tool 40 into the duodenum papilla on the duodenal wall as well as the pancreas duct, common bile duct and the like that are opened at the duodenum papilla.

The endoscope 10 of the side view type may also be referred to as a side view endoscope. Likewise, the endoscope 10 suitable for diagnosis or the like of the duodenum and pancreaticobiliary duct areas may also be referred to as a duodenoscope.

According to the present embodiment, it is possible to provide the cap 50 that may prevent it from being reused by mistake, since the cap 50 is detached from the insertion part 30 by breaking the cover 52 after use. According to the present embodiment, it is possible to provide the endoscope 10 to/from which the elevator 80 and the cap 50 may be attached and detached. According to the present embodiment, it is also possible to provide the endoscope 10 including the elevator 80, which may be subjected to a process such as cleaning with procedures similar to those for a regular endoscope without the elevator 80.

According to the present embodiment, since the pedestal 70 and the cover 52 are separate members, their respective shapes are simple. It is thus possible to manufacture them at lower cost by, for example, injection molding.

For the pivot part, an expandable shape memory alloy (SMA) actuator may also be employed instead of the elevating wire 24. In such a case, one end of the SMA actuator is fixed to the wire fixing part 65 whereas the other end thereof is fixed to the distal end portion 31. A heater is placed around the SMA actuator. The heater is configured to operate in conjunction with the movement of the elevator operation lever 21.

As the heater operates and the SMA actuator contracts, the lever 60 and the elevator 80 pivot. For the pivot part, any other linear actuator may also be employed.

A pivoting actuator such as a small motor may also be employed for the pivot part. The small motor is disposed in the lever chamber 69, and the motor shaft and the lever shaft 63 may be connected with each other to allow the lever 60 to pivot.

In the case where an actuator is employed for the pivot part, the elevator 80 may be operated by a means not using a hand of the user, such as voice control, for example.

The cap 50 may also be provided in the state where the elevator 80 and the cover 52 or the pedestal 70 are temporarily fixed to each other by an adhesive material or the like while the lever connection part 81 faces the opening end 56. Accordingly, the cap 50 which is used in a simple manner may be provided while eliminating the trouble of confirming the orientation of the elevator 80 before the cap 50 is attached to the insertion part 30.

It is also possible for the user to select and use a cap 50 with a specification according to a procedure from multiple types of caps 50 with different specifications. For example, a cap 50 provided with a stopper that restricts the pivotal range of the elevator 80 to be narrow may also be provided. In the case of using a combination of expensive and precise instruments such as an ultrasound probe or ultra-slim endoscope, for example, the narrowing of the pivotal range may prevent such instruments from being damaged by excessive bending.

In the case where the recess 84 has a shape contoured to the profile of the treatment tool tip end 41, the treatment tool 41 is unlikely to sway to the left and right at elevation, and thus tends to be easily operated. Multiple types of caps 50 having elevators 80 with recesses 84 of different shapes may be provided. For example, a cap 50 with a recess 84 having a shape that can easily hold a thin treatment tool 40 may be used to facilitate precise operation of the thin treatment tool 40 such as a guide wire.

Accordingly, the endoscope 10 for which the user may select and use the cap 50 suitable for a purpose may be provided.

The endoscope 10 may be a so-called ultrasound endoscope provided with an ultrasound transducer at the distal end. Here, the cap 50 may preferably have a hole at the bottom through which the ultrasound transducer is inserted. The endoscope 10 may also be an endoscope directed to a lower gastrointestinal tract. The endoscope 10 may also be a so-called rigid endoscope provided with a rigid insertion part 30. The endoscope 10 may also be a so-called industrial endoscope used for inspection of engine, pipework and so forth.

The lever connection part 81 may have the shape of a projection whereas the elevator connection part 61 may be a concave part corresponding to the lever connection part 81.

Embodiment 2

The present embodiment relates to a cap 50 in which a pedestal 70 and a cover 52 are formed in an integral manner. Portions common to those in Embodiment 1 will not be described here.

Figure 17:
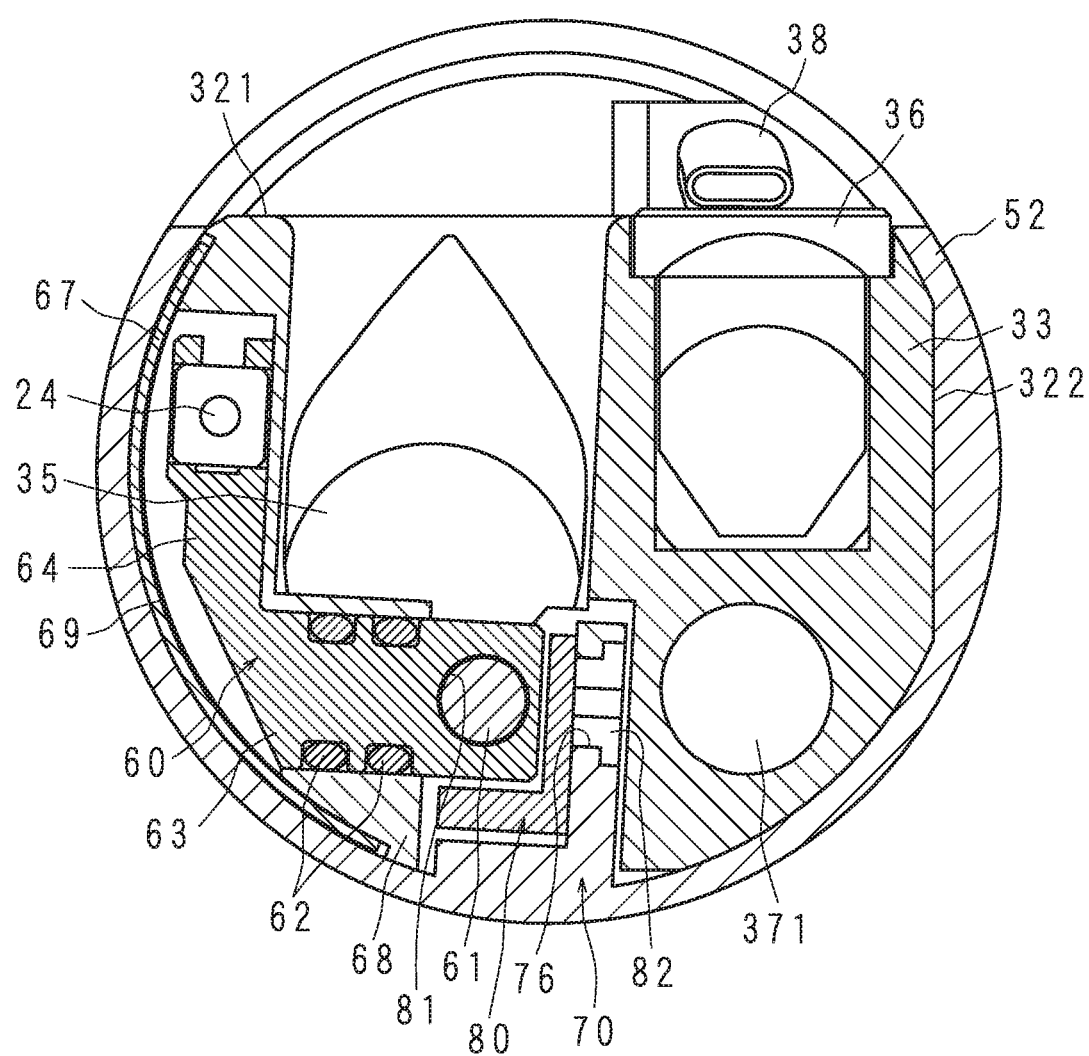
FIG. 17 is section view of an insertion part according to Embodiment 2.

FIG. 17 is a section view of an insertion part 30 according to Embodiment 2. FIG. 17 illustrates a cross section cut at a position similar to the line XI-XI indicated in FIG. 10. In the present embodiment, the pedestal 70 is integrally formed with the inner surface of the cover 52.

For example, a 3D printer may be used to fabricate the cover 52 of this type. The use of the 3D printer capable of printing more than one materials allows for simultaneous fabrication of the pedestal 70 and cover 52, as well as the elevator 80 which can pivot with respect to the pedestal 70.

According to the present embodiment, it is possible to provide the cap 50 with a small number of components to be used.

Embodiment 3

The present embodiment relates to a cap 50 having a cutout 54 at an outer surface of a cover 52. Portions common to those in Embodiment 1 will not be described here.

Figure 18:
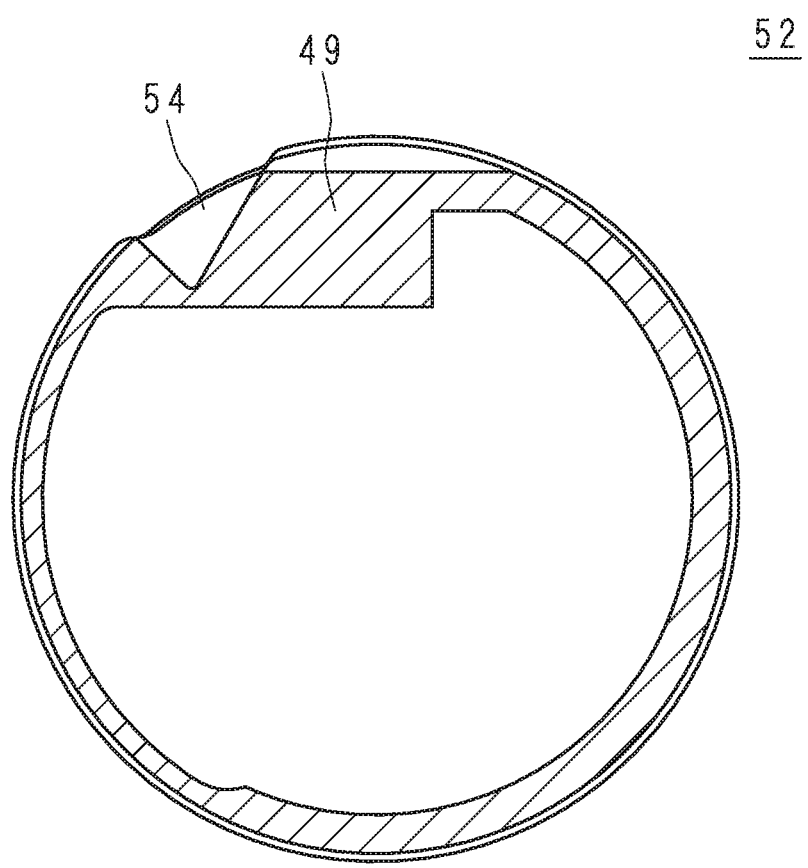
FIG. 18 is a section view of a cover according to Embodiment 3.

FIG. 18 is a section view of the cover 52 according to Embodiment 3. FIG. 18 illustrates a cross section cut at a position similar to the line XIII-XIII indicated in FIG. 10. The cover 52 has a cutout 54 having a substantially triangular cross section at the outer surface thereof. The cutout 54 is a groove formed between the edge of the window part 53 and the opening end 56.

According to the present embodiment, the user may visually and tactually recognize the position of the cutout 54. It is thus possible to provide the cap 50 which allows the user to easily find a position where the cover 52 is breakable. In the case where the cutout 54 is formed at the inner surface of the cover 52 as in Embodiment 1, a mark indicating the position of the cutout 54 may be put on the surface of the cover 52 to obtain an effect similar to that in the present embodiment.

Embodiment 4

The present embodiment relates to a cap 50 having a cutout 54 at inner and outer surfaces of a cover 52. Portions common to those in Embodiment 1 will not be described here.

Figure 19:
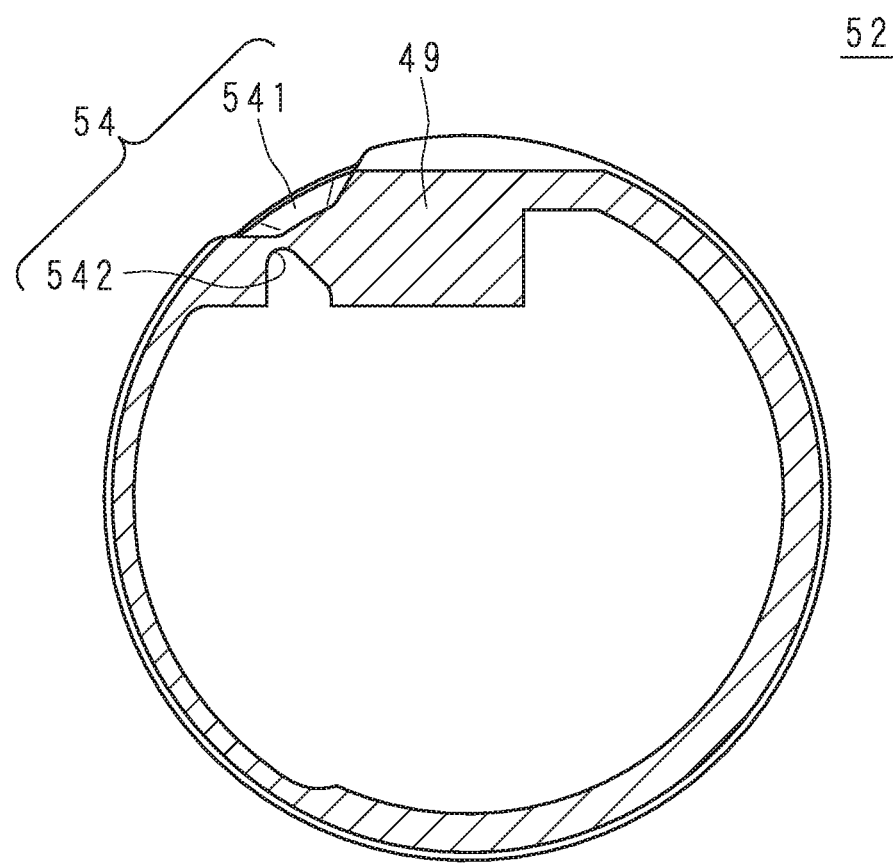
FIG. 19 is a section view of a cover according to Embodiment 4.

FIG. 19 is a section view of the cover 52 according to Embodiment 4. FIG. 19 illustrates a cross section cut at a position similar to the line XIII-XIII indicated in FIG. 10. The cover 52 has two cutouts 54 including a first cutout 541 and a second cutout 542.

The first cutout 541 is a groove having a substantially-triangular cross section formed at the outer surface of the cover 52. The second cutout 542 is a groove having a substantially-triangular cross section formed at the inner surface of the cover 52. The first cutout 541 and the second cutout 542 are grooves formed between the edge of the window part 53 and the opening end 56. The bottom of the groove of the first cutout 541 is proximate to the bottom of the groove of the second cutout 542.

According to the present embodiment, the user may visually and tactually recognize the position of the first cutout 541. The cover 52 has a reduced thickness in the vicinity of the tip end of the first cutout 541. This makes it possible to provide the cap 50 that allows the user to more easily brake and detach the cap 50.

Embodiment 5

The present embodiment relates to a cap 50 having a cutout 54 at the edge of the window part 53. Portions common to those in Embodiment 1 will not be described here.

Figure 20:
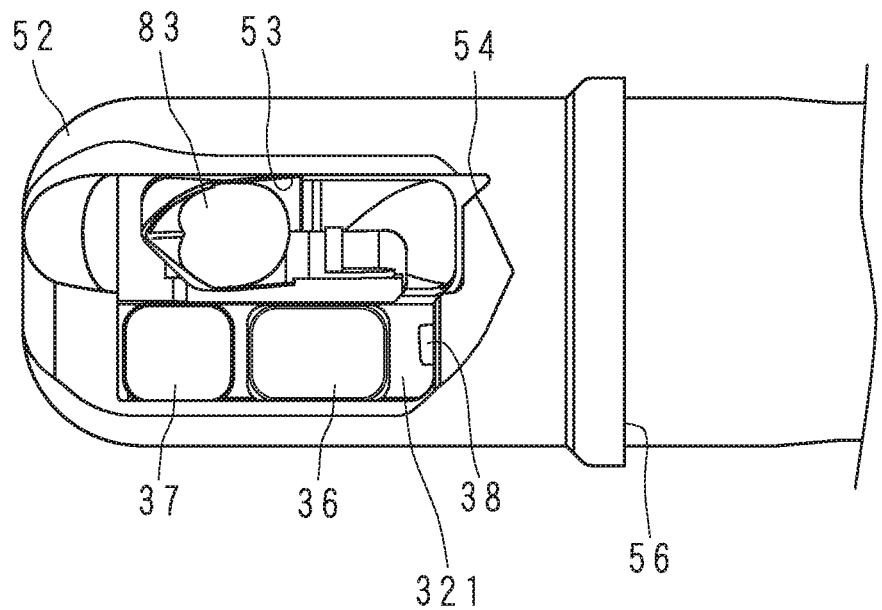
FIG. 20 is a side view of the distal end of an insertion part according to Embodiment 5.

FIG. 20 is a side view of the distal end of an insertion part 30 according to Embodiment 5. FIG. 20 illustrates the distal end of the insertion part 30 to which the cap 50 is attached, when viewed from the window part 53 side. The cover 52 in the present embodiment has a substantially triangular cutout 54 at the edge of the window part 53 on the opening end 56 side.

Since the cutout 54 does not transverse the attachment projection 55 (see FIG. 12) that couples the cover 52 with the tip end portion 31, the cap 50 has a high fixing strength during the use of the endoscope 10. Meanwhile, the user applies a force in a direction of expanding the edge of the window part 53 after finishing the use of the endoscope 10, to break the cover 52 from the tip end of the cutout 54. This can easily detach the cap 50.

According to the present embodiment, it is possible to provide the cap 50 having high fixing strength and being easily detachable by breaking after use.

Embodiment 6

The present embodiment relates to a cap 50 having cutouts 54 at the edge of the window part 53 and at an outer surface of the cover 52. Portions common to those in Embodiment 1 will not be described here.

Figure 21:
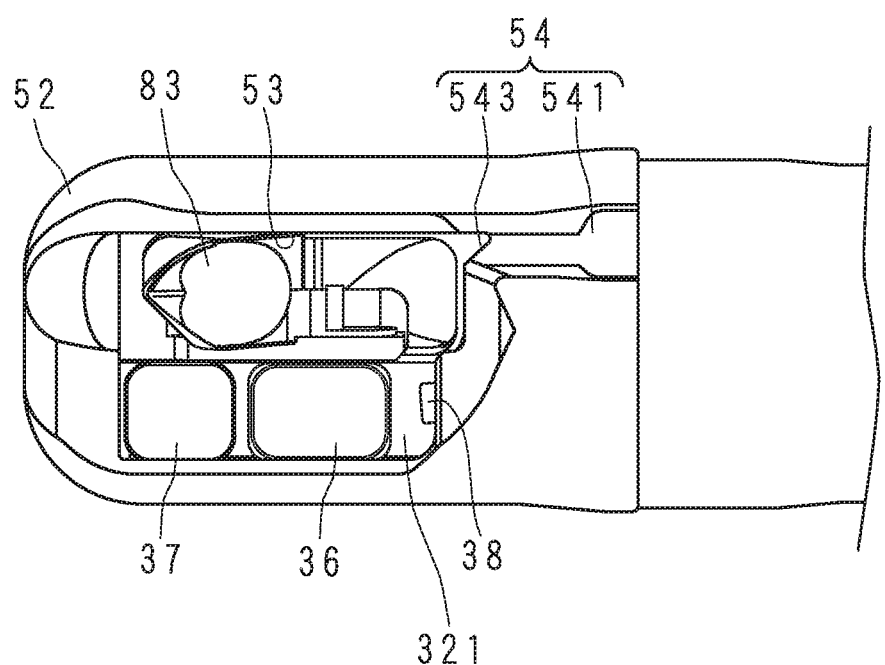
FIG. 21 is a side view of the distal end of an insertion part according to Embodiment 6.

FIG. 21 is a side view of the distal end of an insertion part 30 according to Embodiment 6. FIG. 21 illustrates the distal end of the insertion part 30 to which the cap 50 is attached, when viewed from the window part 53 side. The cover 52 according to the present embodiment has two cutouts 54 including a first cutout 541 and a third cutout 543.

The first cutout 541 is a groove having a substantially-triangular cross section formed at the outer surface of the cover 52. The width of the first cutout 541 is larger in the vicinity of the opening end 56. The first cutout 541 is a groove formed between the edge of the window part 53 and the opening end 56.

The third cutout 543 is a substantially-triangular cutout formed at the edge of the window part 53 on the opening end 56 side. The third cutout 543 is located at a position aligned with the first cutout 541.

According to the present embodiment, the user applies a force in a direction of expanding the edge of the window part 53, to break the cover 52 along the first cutout 541 contiguous to the third cutout 543 from the tip end of the third cutout 543. This makes it even easier to detach the cap 50. It is thus possible to provide the cap 50 that allows the user to easily break and detach the cover 52.

Embodiment 7

The present embodiment relates to a cap 50 having a row of cutouts each having the shape of a small hole aligned between the edge of the window part 53 and the opening end 56. Portions common to those in Embodiment 1 will not be described here.

Figure 22:
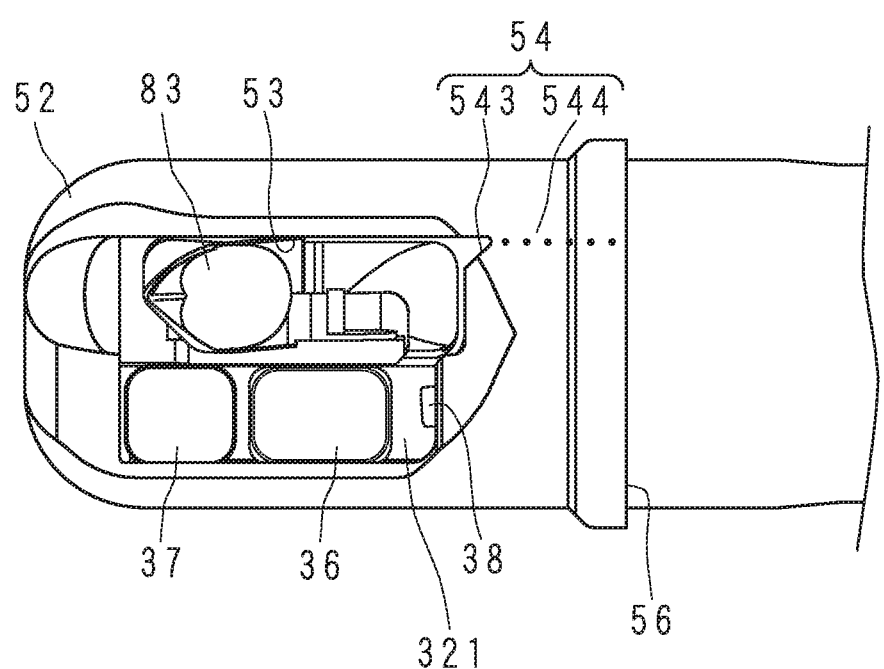
FIG. 22 is a side view of the distal end of an insertion part according to Embodiment 7.

FIG. 22 is a side view of the distal end of an insertion part 30 according to Embodiment 7. FIG. 22 illustrates the distal end of the insertion part 30 to which the cap 50 is attached, when viewed from the window part 53 side. The cover 52 according to the present embodiment has two cutouts 54 including a third cutout 543 and a fourth cutout 544.

The third cutout 543 is a substantially-triangular cutout formed at the edge of the window part 53 on the opening end 56 side. The fourth cutouts 544 correspond to a row of cutouts each having the shape of a small hole aligned between the vicinity of the tip end of the third cutout 543 and the opening end 56. The fourth cutouts 544 may be produced by, for example, laser machining which uses laser beam to open holes in the cover 52.

According to the present embodiment, the user applies a force in a direction of expanding the edge of the window part 53, to break the cover 52 along the fourth cutouts 544 from the tip end of the third cutout 543. This can facilitate detachment of the cap 50. It is thus possible to provide the cap 50 that allows the user to easily break and detach the cover 52.

The fourth cutouts 544 may also correspond to two or more aligned rows of cutouts. The fourth cutouts 544 may also correspond to a row of cutouts not penetrating through the cover 52.

Embodiment 8

The present embodiment relates to the cap 50 having a cutout 54 at an outer surface of the cover 52 and the edge of the opening end 56. Portions common to those in Embodiment 1 will not be described here.

Figure 23:
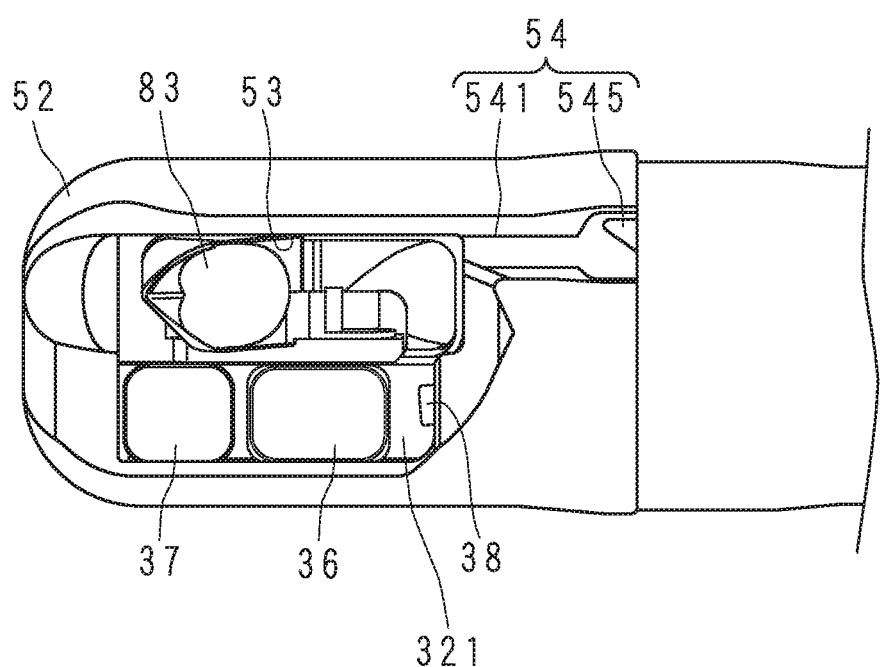
FIG. 23 is a side view of the distal end of an insertion part according to Embodiment 8.

FIG. 23 is a side view of the distal end of an insertion part 30 according to Embodiment 8. FIG. 23 illustrates the distal end of the insertion part 30 to which the cap 50 is attached, when viewed from the window part 53 side. The cover 52 according to the present embodiment has two cutouts 54 including a first cutout 541 and a fifth cutout 545.

The first cutout 541 is a groove having a substantially-triangular cross section formed at the outer surface of the cover 52. The width of the first cutout 541 is larger in the vicinity of the opening end 56. The first cutout 541 is a groove formed between the edge of the window part 53 and the opening end 56.

The fifth cutout 545 is a substantially-triangular cutout formed at the edge of the opening end 56 toward the window part 53. The fifth cutout 545 is located at a position aligned with the first cutout 541.

According to the present embodiment, the user applies a force in a direction of expanding the edge of the fifth cutout 545 from the opening end 56 side, to break the cover 52 along the first cutout 541 from the tip end of the fifth cutout 545. This can further facilitate detachment of the cap 50. It is thus possible to provide the cap 50 that allows the user to more easily break and detach the cover 52.

Embodiment 9

The present embodiment relates to a cap 50 provided in a state where an elevator 80 and a cover 52 or a pedestal 70 are temporarily fixed to each other while a lever connection part 81 faces toward an opening end 56. Portions common to those in Embodiment 1 will not be described here.

Figure 24:
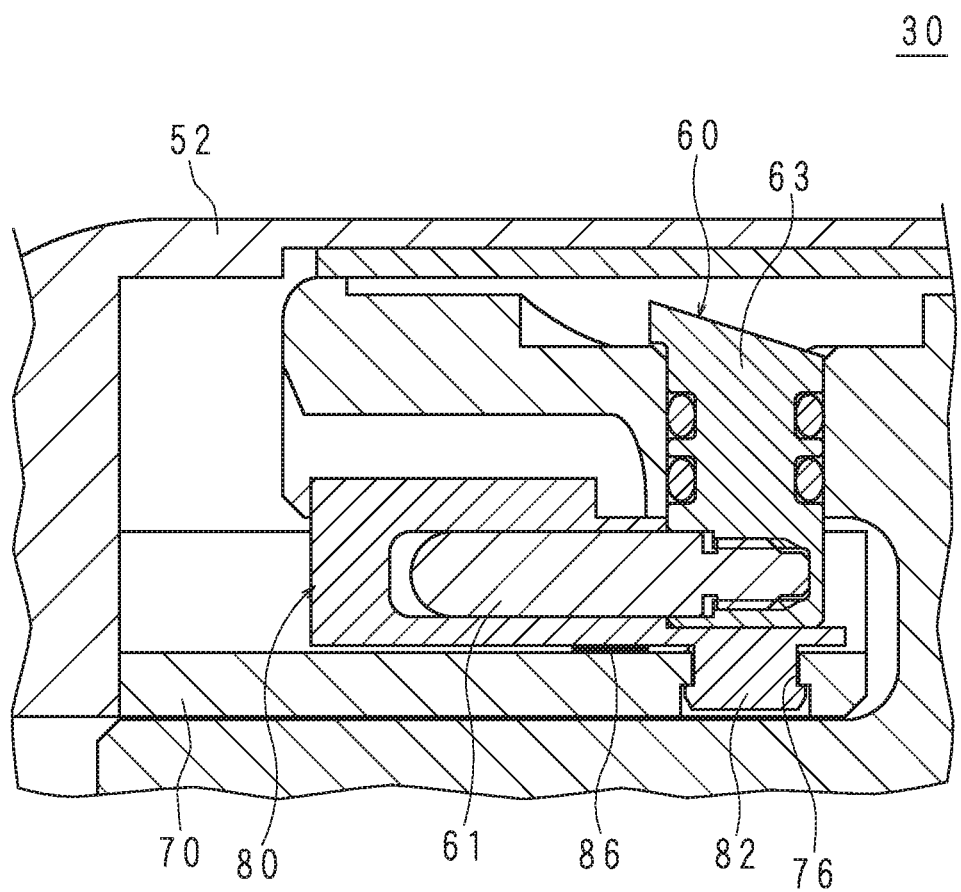
FIG. 24 is an enlarged section view of an insertion part according to Embodiment 9.

FIG. 24 is an enlarged section view of an insertion part 30 according to Embodiment 9. FIG. 24 illustrates an enlarged view around the elevator 80 in a cross section cut at a position similar to the line XII-XII indicated in FIG. 11. The elevator 80 is fixed to the pedestal 70 by a temporary fixing material 86.

The temporary fixing material 86 is, for example, a silicon-based or cyanoacrylic-based adhesive. The temporary fixing material 86 is applied to a predetermined position by a predetermined amount by, for example, a precise dispenser at the time of assembling the cap 50. Thereafter, the temporary fixing material 86 is cured under a predetermined curing condition.

The temporary fixing material 86 has an adhesive strength which is strong enough not to come off during transportation of the cap 50, so as to prevent the elevator 80 from pivoting due to vibration or the like during transportation. This allows the user to easily attach the cap 50 to the insertion part 30 without a trouble of checking and adjusting the orientation of the elevator 80 before attachment.

Furthermore, the temporary fixing material 86 has such an adhesive strength that allows it to be removed by the operation of the elevator operation lever 21. That is, the temporary fixing material 86 has a function of preventing the elevator 80 from pivoting before being attached to the insertion part 30 by temporarily fixing the elevator 80 before use.

After attaching the cap 50 to the insertion part 30, the user operates the elevator operation lever 21 in the state where the window part 53 is facing downward. This removes the temporary fixing material 86 and makes the elevator 80 pivotable. The removed temporary fixing material 86 exits through the window 53 to the outside. The user then uses an endoscope 10 to which the cap 50 is attached.

The temporary fixing material 86 may be an aqueous adhesive which is easily dissolved by being soaked in water or hot water. After the cap 50 is attached to the insertion part 30, the user may soak the tip end of the endoscope 10 in water or hot water to remove the temporary fixing material 86.

According to the present embodiment, the cap 50 which is to be easily attached to the endoscope 10 by the user may be provided.

It is noted that the temporary fixing material 86 may be located at any position where the elevator 80 and the cover 52 or pedestal 70 are fixed to each other and where the elevator 80 may be prevented from pivoting.

Embodiment 10

The present embodiment relates to a cap 50 provided in a state where an elevator shaft 82 and an elevator attachment hole 76 are temporarily fixed to each other. Portions common to those in Embodiment 1 will not be described here.

Figure 25:
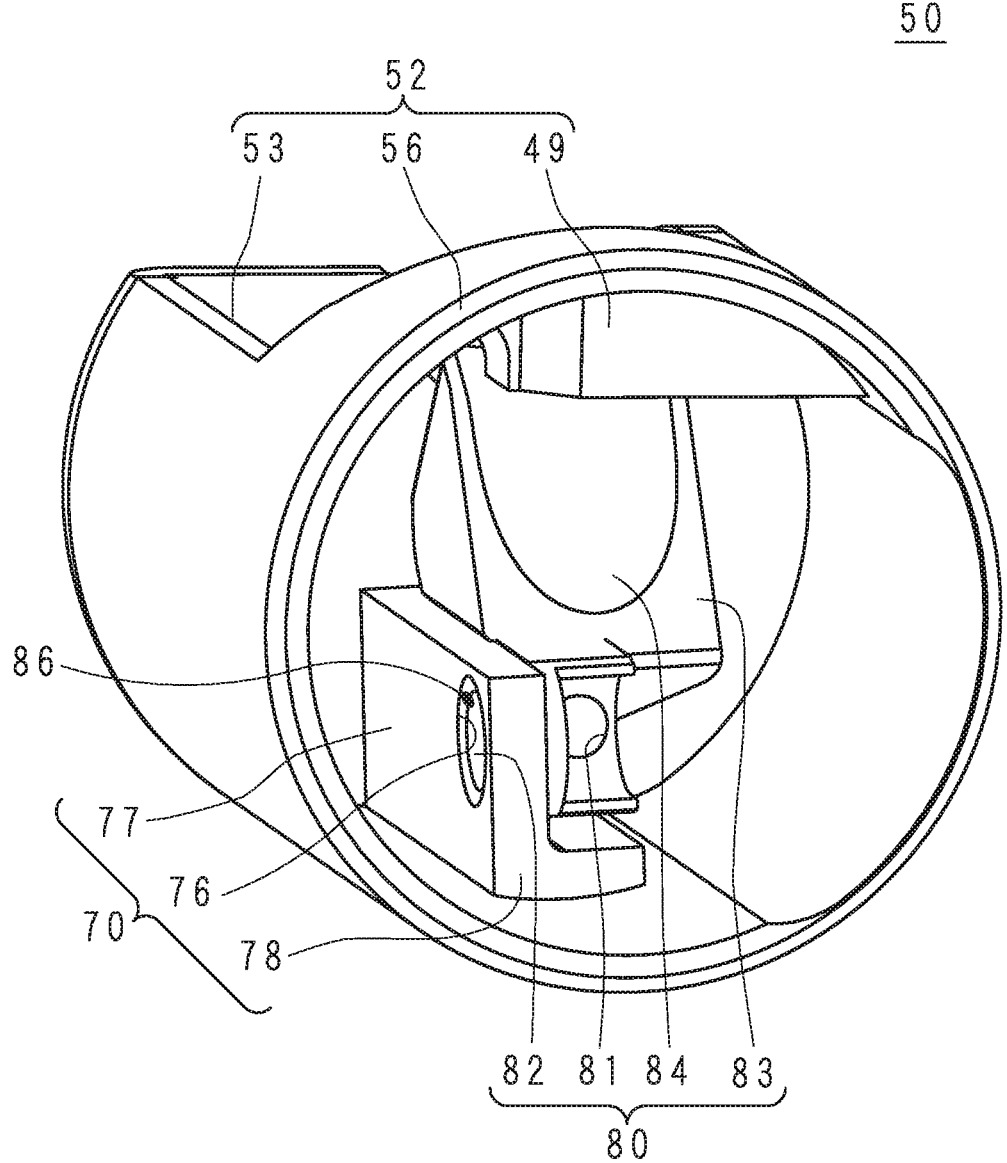
FIG. 25 is a perspective view of a cap according to Embodiment 10.

FIG. 25 is a perspective view of a cap 50 according to Embodiment 10. FIG. 25 is a perspective view of a cap 50 when viewed from the attachment side to the endoscope 10.

A temporary fixing material 86 is so located as to connect the end face of the elevator shaft 82 and the inner surface of the elevator attachment hole 76. The temporary fixing material 86 is an adhesive with high viscosity. The temporary fixing material 86 may be provided at two or more locations. The temporary fixing material 86 may be provided circumferentially along the edge of the end face of the elevator shaft 82. The temporary fixing material 86 may be provided to cover the end face of the elevator shaft 82.

After attaching the cap 50 to the insertion part 30, the user operates the elevator operation lever 21. This removes the temporary fixing material 86 and makes the elevator 80 pivotable. The removed temporary fixing material 86 remains in a space between the pedestal 70 and the distal end portion 31 of the endoscope 10.

According to the present embodiment, the cap 50 which is to be easily attached to the endoscope 10 by the user may be provided. According to the present embodiment, the temporary fixing material 86 remains inside the cap 50 until the cap 50 is detached from the endoscope 10 after use. It is therefore possible to provide the cap 50 which does not litter the temporary fixing material 86 at the stage of preparing for an endoscopy.

Embodiment 11

The present embodiment relates to a cap 50 in which a temporary fixing material 86 has the shape of a tape. Portions common to those in Embodiment 1 will not be described here.

Figure 26:
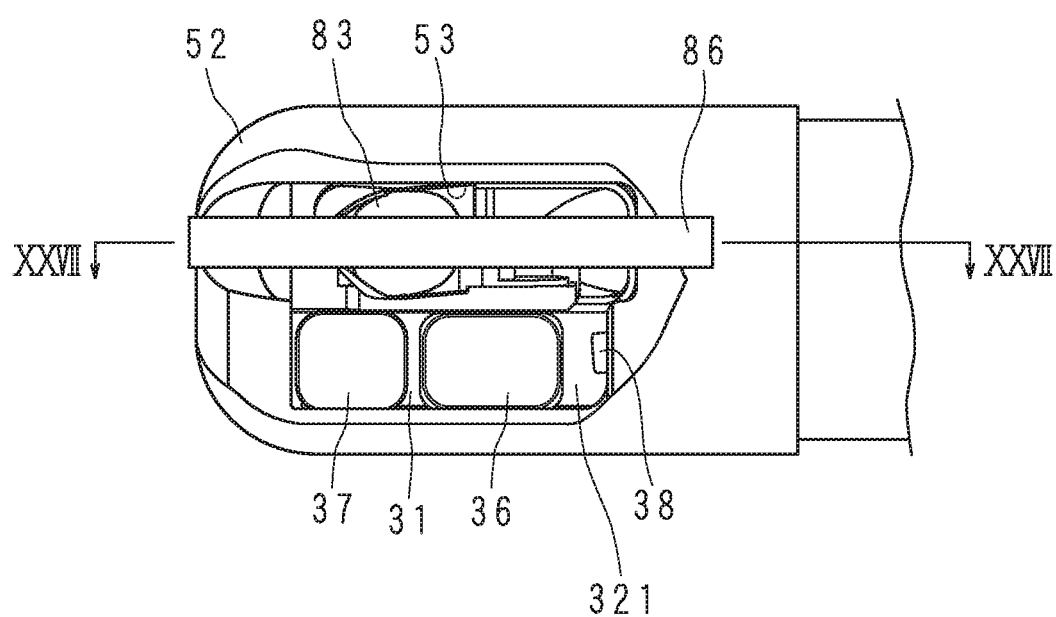
FIG. 26 is a side view of the distal end of an insertion part according to Embodiment 11.
Figure 27:
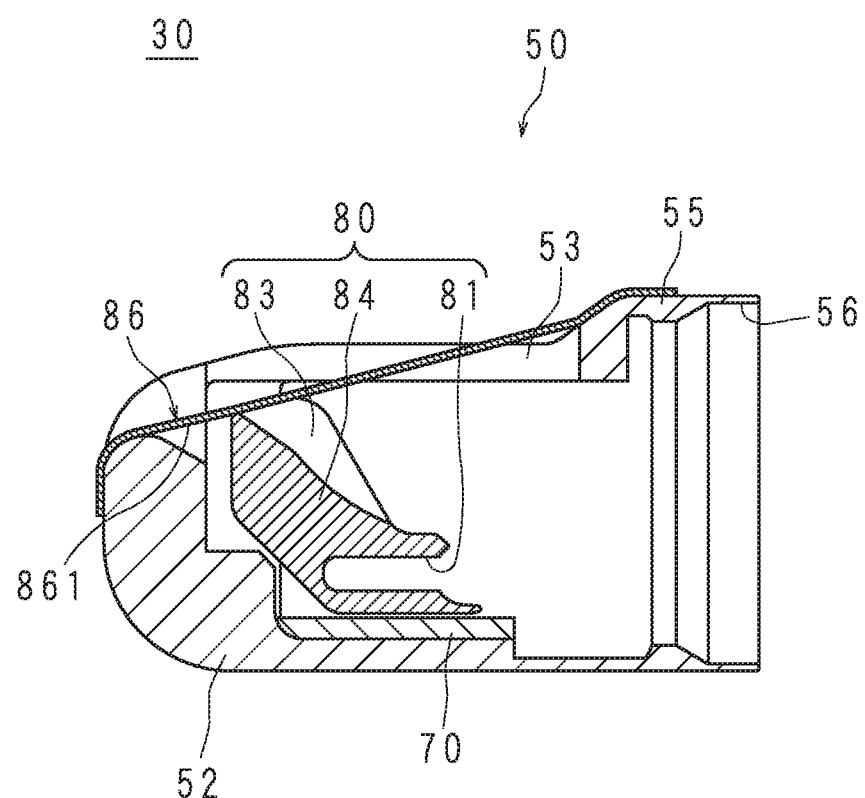
FIG. 27 is a section view of the insertion part taken along the line XXVII-XXVII in FIG. 26.

FIG. 26 is a side view of the distal end of an insertion part 30 according to Embodiment 11. FIG. 26 illustrates the distal end of the insertion part 30 immediately after the cap 50 is attached thereto, when viewed from the window part 53 side. FIG. 27 is a section view of the insertion part 30 taken along the line XXVII-XXVII in FIG. 26.

The temporary fixing material 86 according to the present embodiment is a so-called adhesive tape, which is a tape-shaped paper or resin base material with one surface applied with an adhesive. In the following description, the surface to which the adhesive is applied is referred to as an adhesive surface 861. It is noted that the temporary fixing material 86 may have a buffer material such as sponge between the base material and adhesive. The adhesive may also be a foam material.

The temporary fixing material 86 covers a portion of the window part 53 along the insertion direction in the case where the cap 50 is attached to the endoscope 10. The adhesive surface 861 is adhered to the surface of the cover 52 at both ends of the temporary fixing material 86. An end of the elevating part 83 is adhered to the adhesive surface 861. This prevents the elevator 80 from pivoting.

After the cap 50 is attached to the insertion part 30, the user peels off the temporary fixing material 86 from the cap 50. This allows the elevator 80 to be pivotable.

According to the present embodiment, the cap 50 which is easily recognized by the user that the temporary fixing material 86 is removed therefrom may be provided.

The technical features (components) described in each example embodiment may be combined with one another, and such combinations may form new technical features.

It is to be noted that, as used herein and in the appended claims, the singular forms "a", "an", and "the" include plural referents unless the context clearly dictates otherwise.

It should be understood that the embodiments disclosed herein are illustrative and non-restrictive in every respect. Since the scope of the present invention is defined by the appended claims rather than by the description preceding them, all changes that fall within metes and bounds of the claims, or equivalence of such metes and bounds thereof are therefore intended to be embraced by the claims.

In relation to the embodiments including Embodiments 1 to 11 described above, the following clauses will further be disclosed.

1. An endoscope cap attachable to and detachable from an endoscope including a lever pivotally provided at a distal end of an insertion part of an endoscope and a pivot part causing the lever to pivot, comprising:
    a bottomed cylindrical cover having an opening end; and
    an elevator pivotally supported at an inside of the cover, connected to the lever when the cover is attached to the endoscope, and pivoting in response to pivoting of the lever.

2. The endoscope cap according to clause 1, wherein
    the cover has a window part at a side surface, and
    the elevator includes an elevator shaft pivotally supported by the cover and a lever connection part located at the opening end side and connectable to the lever.

3. The endoscope cap according to clause 2, wherein the elevator is pivotable in a direction of changing a distance between the elevator and the window part.

4. The endoscope cap according to clause 2 or 3, wherein the cover has a cutout contiguous to the window part.

5. The endoscope cap according to any one of clauses 2 to 4, further comprising a pedestal fixed to an inside of the cover, wherein the elevator shaft is pivotally supported at the inner side of the cover through the pedestal.

6. An endoscope, comprising:
    a hollow lever chamber protruding from a part of a distal end of an insertion part in an insertion direction and including a support wall along the insertion direction; and
    a lever having a lever shaft penetrating the support wall and an elevator connection part located outside the lever chamber and exposed to a surface, the lever being pivotable around the lever shaft.

7. The endoscope according to clause 6, comprising an endoscope cap including:
    a bottomed cylindrical cover having an opening end; and
    an elevator pivotally supported at an inner side of the cover, connected to the lever when the cover is attached to the endoscope, and pivoting in response to pivoting of the lever.

8. A method of manufacturing an endoscope cap, comprising:
    inserting an elevator shaft of an elevator into a pedestal;
    inserting the pedestal together with the elevator into a bottomed cylindrical cover having an opening end through the opening end; and
    fixing the cover and the pedestal to each other.

9. A method of using an endoscope cap, comprising:
    preparing an endoscope including a lever pivotally provided at a distal end of an insertion part of an endoscope and a pivot part pivoting the lever; and
    attaching an endoscope cap to the endoscope, the endoscope cap including: a bottomed cylindrical cover having an opening end; and an elevator pivotally supported at an inner side of the cover, connected to the lever when the cover is attached to the endoscope, and pivoting in response to pivoting of the lever.

10. A method of using the endoscope cap according to clause 9, comprising:
    breaking the cover through a cutout formed at the cover; and
    removing the endoscope cap from the endoscope after breaking.

11. An endoscope cap, comprising:
    a cover which is attachable to and detachable from a distal end of an insertion part of an endoscope; and
    a cutout formed at the cover,
    wherein the cover may be detached from the endoscope by breaking the cover through the cutout.

12. The endoscope according to clause 11, comprising an elevator located inside the cover.

13. The endoscope cap according to clause 12, wherein
    the endoscope includes a lever pivotally provided at a distal end of an insertion part and a pivot part causing the lever to pivot,
    the endoscope cap comprises a pedestal fixed to an inside of the cover and having an elevator attachment hole,
    the cover has a bottomed cylindrical shape having an opening end and a window part opened at a side surface, the opening end being attachable to and detachable from a distal end of the insertion part of the endoscope,
    the cutout is contiguous to the window part, and
    the elevator is located inside the cover and having an elevator shaft inserted into the elevator attachment hole, an elevating part protruding in a direction intersecting the elevator shaft, and a lever connection part located at the opening end side of the elevating part and connected to the lever, the elevator being pivotable around the elevator shaft with respect to the pedestal.

14. The endoscope cap according to clause 13, wherein the elevator is pivotable in a direction of changing a distance between the elevator and the window part.

15. The endoscope cap according to clause 13 or 14, wherein the cover is integrally formed with the pedestal.

16. The endoscope cap according to any one of clauses 13 to 15, wherein the cutout is a triangle cutout provided contiguous to an edge of the window part toward the opening end.

17. The endoscope cap according to any one of clauses 13 to 16, wherein the cutout is a groove-shaped cutout formed between the opening end and the window part.

18. The endoscope cap according to clause 17, wherein the cutout is formed at an outer surface of the cover.

19. The endoscope cap according to clause 17, wherein the cutout is formed at an inner surface of the cover.

20. The endoscope cap according to clause 17, wherein the cutout is formed at each of an inner surface and an outer surface of the cover.

21. The endoscope cap according to any one of clauses 13 to 20, wherein the cover has an attachment projection extending along an edge of an inner surface on the opening end side.

22. An endoscope cap attachable to and detachable from an endoscope including a lever pivotally provided at a distal end of an insertion part of an endoscope and a pivot part causing the lever to pivot, comprising:
    a cylindrical cover;

an elevator pivotally supported at an inside of the cover, connected to the lever and pivoting in response to pivoting of the lever; and a temporary fixing material temporarily fixing the elevator before the endoscope cap is mounted to the endoscope so as to prevent the elevator from pivoting.

23. The endoscope cap according to clause 22, wherein the temporary fixing material fixes the elevator and the cover to each other.

24. The endoscope cap according to clause 22 or 23, wherein the temporary fixing material is removed from the elevator or the cover by pivoting the lever.

25. The endoscope cap for single use according to any one of clauses 13 to 24, wherein the cap is detached from the endoscope and is discarded after being used for one case.

26. An endoscope, comprising:

a hollow lever chamber protruding from a part of a distal end of an insertion part in an insertion direction and including a support wall along the insertion direction; and a pivot part operated remotely from an outside of the lever chamber; and a lever including a lever shaft penetrating the support wall, a pivot connection part located contiguous to the lever shaft, accommodated in the lever chamber and connected to the pivot part, and an elevator connection part formed outside the lever chamber and exposed to a surface, the lever being pivotable around the lever shaft.

27. The endoscope according to clause 26, comprising an endoscope cap including: a bottomed cylindrical cover having an opening end, a window part provided at a side surface and a cutout contiguous to the window part, the opening end being attachable to and detachable from a distal end of an insertion part of the endoscope; a pedestal fixed to an inside of the cover and having an elevator attachment hole; an elevator located inside the cover and having an elevator shaft inserted into the elevator attachment hole, an elevating part protruding in a direction intersecting the elevator shaft and a lever connection part located at the opening end side of the elevating part, the elevator being pivotable around the elevator shaft with respect to the pedestal, wherein in a case where the opening end is attached to the distal end of the insertion part, the elevator connection part is connected to the lever connection part, and the elevator shaft is arranged coaxially with the lever shaft.

28. The endoscope according to clause 27, wherein the lever connection part is a concave part opened toward the opening end, and the elevator connection part is a projection corresponding to the lever connection part.

29. The endoscope according to clause 27 or 28, wherein the lever connection part is a projection protruding toward the opening end, and the elevator connection part is a concave part corresponding to the lever connection part.

30. The endoscope according to any one of clauses 27 to 29, wherein the pivot connection part protrudes in a direction intersecting with the lever shaft.

31. The endoscope according to clause 30, wherein the pivot part is an elevating wire penetrating the insertion part.

32. A method of manufacturing an endoscope cap, comprising:

inserting, into an elevator attachment hole formed at a pedestal, an elevator shaft of an elevator including the elevator shaft, an elevating part protruding in a direction intersecting the elevator shaft and a lever connection part located at the elevator shaft side of the elevator;

inserting the pedestal together with the elevator through the opening end into a bottomed cylindrical cover that has an opening end, a window part provided at a side surface, and a cutout contiguous to the window part, and that is attachable to and detachable from a distal end of an insertion part of the endoscope; and fixing the cover and the pedestal to each other.

33. The method of manufacturing an endoscope cap according to clause 32, wherein the insertion direction of the elevator shaft intersects with the insertion direction of the pedestal.

What is claimed is:

1. An endoscope cap attachable to and detachable from an endoscope including a lever pivotally provided at a distal end of an insertion part of an endoscope and a pivot part causing the lever to pivot, comprising:

a bottomed cylindrical cover having an opening end, a window part opened at a side surface and a cutout contiguous to the window part, the opening end being attachable to and detachable from a distal end of an insertion part of the endoscope;

a pedestal fixed to an inside of the cover and having an elevator attachment hole; and an elevator located inside the cover and having an elevator shaft inserted into the elevator attachment hole, an elevating part protruding in a direction intersecting the elevator shaft, and a lever connection part located at the opening end side of the elevating part and connected to the lever, the elevator being pivotable around the elevator shaft with respect to the pedestal, wherein before being attached to the endoscope, the cover is formed to break, without use of a cutting tool and while the cover is attached to the endoscope, at the cutout and along a single fracture line by inserting a user's own finger through the window part, to become detachable from the endoscope as a single piece.

2. The endoscope cap according to claim 1, wherein the elevator is pivotable in a direction of changing a distance between the elevator and the window part.

3. The endoscope cap according to claim 1, wherein the cover is integrally formed with the pedestal.

4. The endoscope cap according to claim 1, wherein the cutout is a triangle cutout provided contiguous to an edge of the window part toward the opening end.

5. The endoscope cap according to claim 1, wherein the cutout is a groove-shaped cutout formed between the opening end and the window part.

6. The endoscope cap according to claim 5, wherein the cutout is formed at an outer surface of the cover.

7. The endoscope cap according to claim 5, wherein the cutout is formed at an inner surface of the cover.

8. The endoscope cap according to claim 5, wherein the cutout is formed at each of an inner surface and an outer surface of the cover.

9. The endoscope cap according to claim 1, wherein the cover has an attachment projection extending along an edge of an inner surface on the opening end side.

10. An endoscope cap for single use according to claim 1, wherein the cap is detached from the endoscope and is discarded after being used for one case.

11. The endoscope cap accordingly to claim 1, wherein the cutout is a groove.

* * * * *